United States Patent
Schwitter et al.

(10) Patent No.: US 9,676,793 B2
(45) Date of Patent: Jun. 13, 2017

(54) CO-CRYSTALS OF 5-AMINO-2-OXOTHIAZOLO[4,5-D] PYRIMIDIN-3(2H)-YL-5-HYDROXYMETHYL TETRAHYDROFURAN-3-YL ACETATE AND METHODS FOR PREPARING AND USING THE SAME

(71) Applicant: Hoffmann-La Roche Inc., Little Falls, NJ (US)

(72) Inventors: Urs Schwitter, Basel (CH); Fritz Bliss, Basel (CH); Michael Kammerer, Basel (CH); Florence Tixeront, Basel (CH)

(73) Assignee: Hoffmann-LaRoche Inc., Little Falls, NJ (US)

( * ) Notice: Subject to any disclaimer, the term of this patent is extended or adjusted under 35 U.S.C. 154(b) by 0 days.

(21) Appl. No.: 14/976,713

(22) Filed: Dec. 21, 2015

(65) Prior Publication Data
US 2016/0176899 A1   Jun. 23, 2016

Related U.S. Application Data

(60) Provisional application No. 62/095,910, filed on Dec. 23, 2014.

(51) Int. Cl.
| | |
|---|---|
| C07D 513/04 | (2006.01) |
| C07C 55/12 | (2006.01) |
| C07C 55/08 | (2006.01) |
| C07C 57/15 | (2006.01) |
| C07C 55/14 | (2006.01) |
| C07C 59/06 | (2006.01) |
| C07C 59/185 | (2006.01) |

(52) U.S. Cl.
CPC ............ *C07D 513/04* (2013.01); *C07C 55/08* (2013.01); *C07C 55/12* (2013.01); *C07C 55/14* (2013.01); *C07C 57/15* (2013.01); *C07C 59/06* (2013.01); *C07C 59/185* (2013.01)

(58) Field of Classification Search
CPC ....... C07D 513/04; C07C 55/12; C07C 55/08; C07C 57/15
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 7,928,085 | B2 | 4/2011 | Kucera et al. |

FOREIGN PATENT DOCUMENTS

| | | | |
|---|---|---|---|
| WO | WO2008140549 | 11/2008 | |
| WO | 2009/026292 A1 | 2/2009 | |
| WO | WO 2009026292 A1 * | 2/2009 | ............. A61K 31/40 |

OTHER PUBLICATIONS

Ning Qiao et al., "Pharmaceutical cocrystals: An overview", International Journal of Pharmaceutics Elsevier BV, NL, vol. 419, No. 1, Jul. 23, 2011 (Jul. 23, 2011), pp. 1-11, XP028306606, ISSN: 0378-5173.

Feb. 19, 2016 International Search Report and Written Opinion issued in International Application No. PCT/IB2015/059861.

* cited by examiner

*Primary Examiner* — Kahsay Habte
(74) *Attorney, Agent, or Firm* — Mintz Levin Cohn Ferris Glovsky and Popeo, P.C.

(57) ABSTRACT

Co-crystals of Formula I compounds and their pharmaceutical compositions are novel therapeutics for the treatment of diseases, such as human immunodeficiency virus (HIV) infection, hepatitis B virus (HBV) infection, hepatitis C virus (HCV) infection and cancer. The co-crystal are more stable to oxidation and aqueous degradation, have a better pharmacokinetic profile and superior biological activity than the corresponding tosylate salt form of Formula I compound.

19 Claims, 5 Drawing Sheets

CO-CRYSTALS OF 5-AMINO-2-OXOTHIAZOLO[4,5-D] PYRIMIDIN-3(2H)-YL-5-HYDROXYMETHYL TETRAHYDROFURAN-3-YL ACETATE AND METHODS FOR PREPARING AND USING THE SAME

CROSS REFERENCE TO RELATED APPLICATIONS

This application claims the benefit of U.S. Provisional Application No. 61/095,910 filed Dec. 23, 2014.

FIELD OF INVENTION

The present invention relates to co-crystals of 5-amino-2-oxothiazolo[4,5-d]pyrimidin-3(2H)-yl-5-hydroxymethyl tetrahydrofuran-3-yl acetate and an organic acid, the synthesis of the co-crystals, and their use for the treatment of pathological disorders, particularly Hepatitis B (HBV) infection.

BACKGROUND OF THE INVENTION

Nucleoside analogues are molecules that act like or mimic natural nucleosides in DNA synthesis. Compounds within the category "nucleoside analogs" are important therapeutic agents for the treatment of cancer, viral infection and immunosuppressive disorders. Nucleoside analogs exert their therapeutic effect by inhibiting DNA synthesis. After entry into a cell, nucleoside analogs are phosphorylated to the corresponding mono-, di-, or triphosphates. Triphosphate nucleoside analogs inhibit cell division by terminating DNA transcription.

Nucleoside analogs also have a well-established regulatory history, with several nucleoside analogs currently approved by the US Food and Drug Administration (FDA) for the treatment of diseases, such as human immunodeficiency virus (HIV) infection, hepatitis B virus (HBV) infection, hepatitis C virus (HCV) infection and cancer.

The hepatitis B virus (HBV) is second only to tobacco as a cause of human cancer. The mechanism by which HBV induces cancer is unknown. It is postulated that HBV infection may directly trigger tumor development, or indirectly trigger tumor development through chronic inflammation, cirrhosis, and cell regeneration associated with the infection. Persons infected by HBV suffer from acute hepatitis and liver damage, resulting in abdominal pain, jaundice and elevated blood levels of certain liver enzymes. While patients typically recover from acute HBV infection, the virus can continue to replicate indefinitely causing a chronic persistent hepatitis which is one of the main causes of hepatocellular carcinoma, a primary liver cancer.

3TC (lamivudine), interferon alpha-2b, peginterferon alpha-2a, hepsera (adefovir dipivoxil), baraclude (entecavir), and Tyzeka (Telbivudine) are currently FDA-approved drugs for treating HBV infection. However, many of these drugs have severe side effects and viral resistance develops rapidly in patients treated with these drugs. Other disadvantages of commercially available nucleoside analogs include without limitation the difficulty associated with their manufacture utilizing multi-step synthetic protocols that require time-consuming, costly purification, as well as challenges associated with their stability during storage and the ability to inhibit viral replication without damaging the host cells.

SUMMARY OF THE INVENTION

The present invention provides co-crystals as therapeutic agents for treating diseases and disorders, such as cancers, viral infections and disorders associated with improper immune function.

In one embodiment, the invention provides a co-crystal comprising at least two components: (A) a compound according to Formula I or a pharmaceutically acceptable stereoisomer, or tautomer thereof; and

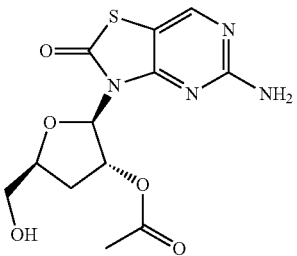

I (B) a co-crystal former.

The co-crystal formers are organic acids. Illustrative of organic acids that can be used as co-crystal formers are fumaric acid, malonic acid, glutaric acid, adipic acid, α-keto glutaric acid and anthranilic acid. According to one embodiment the co-crystal former is glutaric acid, while for some other embodiments the co-crystal former can be an organic acid selected from malonic acid, adipic acid, or fumaric acid.

Co-crystals according to the present invention can comprise a Formula I compound and malonic acid, a Formula I compound and fumaric acid, a Formula I compound and glutaric acid, a Formula I compound and adipic acid, a Formula I compound and anthranilic acid, or a Formula I compound and α-keto glutaric acid. The ratio of the Formula I compound to co-crystal former for the inventive co-crystals can be 1:1, 1:2, or 2:1.

The inventive co-crystals are crystalline and have characteristic X-ray powder diffraction peaks at a diffraction angle of 2θ as further illustrated in Table 2. The inventive co-crystals were further characterized by IR absorption spectroscopy.

In one embodiment, the invention provides a pharmaceutical composition comprising a pharmaceutically acceptable carrier or diluent and a co-crystal comprising at least two components: (A) a compound according to Formula I or a pharmaceutically acceptable stereoisomer or tautomer thereof and (B) and a co-crystal former. According to an embodiment, the co-crystal of the inventive pharmaceutical composition comprises a Formula I compound and glutaric acid as the co-crystal former.

According to another embodiment, the invention provides a method for treating a disease or condition by administering to a subject in need thereof a therapeutically effective amount of the co-crystal according to claim 1. Illustrative of diseases or conditions treated using the inventive co-crystal are those selected from cancer, inflammation, or Hepatitis B infection.

According to an embodiment of this method, the co-crystal is administered in combination with a therapeutically effective amount of a second therapeutic agent selected from the group consisting of antibiotics, antiemetic agents, anti-inflammatory agents, antiviral agents, anticancer agents, immunomodulatory agents, α-interferon, β-interferon, pegylated α-interferon, pegylated β-interferon, ribavirin, alkylating agents, hormones, cytokines, polymerase inhibitors, and toll receptor-like modulators.

Co-crystals in accordance with the invention are synthesized by combining a solution or a suspension of a co-crystal former with a solution or a suspension of a Formula I compound or a pharmaceutically acceptable stereoisomer or tautomer thereof to obtain a co-crystallization solution, followed by supersaturating the co-crystallization solution to initiate formation of co-crystals.

Solvents used to solubilize the co-crystal former a Formula I compound include organic solvents, water, or a mixture of water and an organic solvent. Illustrative of the class organic solvents suitable for solubilizing the co-crystal former include without limitation methanol, ethanol, propanol, isopropanol, isopropyl acetate, hexane, heptane, toluene, acetone, acetonitrile, dioxane, tetrahydrofuran (THF), ethyl acetate, or combinations thereof.

DETAILED DESCRIPTION

Figure 1:
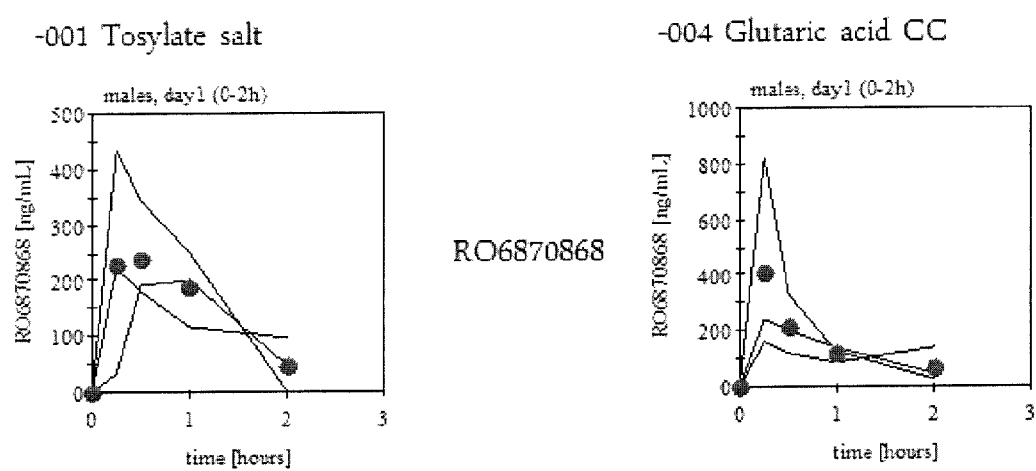
FIG. 1—In vivo pharmacokinetics of an exemplary glutaric acid co-crystal in accordance with the invention. The figure illustrates the average plasma concentration in cynomolgus monkeys after an oral administration of the glutarate co-crystal or tosylate salt of the Formula I compound at a dose of 10 mg/Kg.

The present invention provides co-crystals that comprise a Formula I compound and an organic acid as the co-crystal former. The inventive co-crystals and their pharmaceutical compositions are useful in treating or preventing viral infections, cancer and diseases or conditions that are associated with improper immune function.

It should be noted that the term "comprising" (and its grammatical variations) is used in the inclusive sense of "having" or "including" and not in the exclusive sense of "consisting only of". The terms "a," "an" and "the" as used herein are understood to encompass the plural as well as the singular.

The phrases "active pharmaceutical ingredient" or "API" refer to a substance, for example a compound or a biologic in a pharmaceutical composition that elicits a biological activity.

Within the context of the present invention the term "co-crystal" refers to a crystalline molecular complex comprised of two or more compounds. Pharmaceutical co-crystals contain a drug substance and one or more additional molecules that are present in the same crystal. The two or more compounds of a co-crystal can be in a solid form at room temperature. Each compound has its own distinctive physical characteristics, such as structure, melting point and heats of fusion. The term "co-crystal" also refers to a crystalline material comprised of two or more compounds that may each be in a liquid form at room temperature but form a crystalline material when combined under conditions that promote co-crystallization. Co-crystals according to the present invention further encompass a crystalline material that is obtained by combining a compound that is a solid at room temperature with a compound that is a liquid at room temperature under conditions suitable to promote co-crystallization. In some aspects of the present invention the inventive co-crystals are obtained by combining a solvate of a Formula I compound with a co-crystal former or by combining a Formula I compound with a solvate of a co-crystal former under conditions suitable to promote co-crystallization.

The phrase "co-crystal former" refers to the additional compound or guest compound that is present along with drug within the same crystalline molecular complex of a co-crystal. Any molecule that can participate in donor-acceptor interactions with the drug may be used as a co-crystal former. Compounds illustrative of the class "co-crystal formers" include without limitation organic acids, organic bases, alcohols, phenols esters and cyclodextrins. For instance, the co-crystal former may be saccharin, nicotinamide 4-hydroxybenzoic acid, benzoic acid, glutaric acid, fumaric acid, malonic acid, adipic acid, α-keto glutaric acid, anthranilic acid. or methyl paraben.

Within the context of the invention, the term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, preferably a human, including chimeric and transgenic animals and mammals.

The term a "therapeutically effective amount" refers to an amount of the compound of the invention sufficient to provide a benefit in the treatment or prevention of disease, to delay or minimize symptoms associated with disease, or to cure or ameliorate the disease or infection or causes thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

Some compounds described herein can have asymmetric centers and therefore can exist as enantiomers and diastereomers. A compound of the invention can be in the form of a single enantiomer (optical isomer), a diastereomer, or as a mixture of enantiomers, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. Those skilled in the art of organic synthesis will know if the compounds are prepared as single enantiomers from the methods used to prepare them.

Co-Crystals 5-amino-2-oxothiazolo[4,5-d]pyrimidin-3 (2H)-yl-5-hydroxymethyl tetrahydrofuran-3-yl acetate illustrated below as Formula I is a 3'-deoxyadenosine analog that exists as an amorphous powder in the free base form.

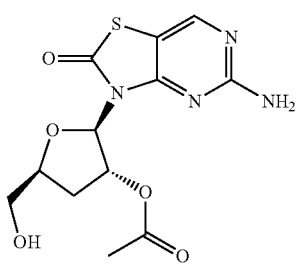 [SMILES: CC(=O)O[C@@H]1C[C@@H](CO)O[C@H]1n1c(=O)sc2cnc(N)nc21]

The free base, however, has poor chemical stability and with no suitable manufacturing process to consistently synthesize pharmaceutical grade material, the free base is unsuitable as a pharmaceutical agent. To address these drawbacks, the p-toluenesulfonic acid (tosylate) salt of the free base was synthesized as described in U.S. Pat. No. 7,928,085. As disclosed in this patent, the crystalline nature of the tosylate salt has certain advantages over the free base. For example, the tosylate salt has greater stability and aqueous solubility than the free base. Thus the tosylate salt was considered to be a more suitable agent than the free base for formulating pharmaceutical compositions having a low residual solvent content.

While the tosylate salt form of 5-amino-2-oxothiazolo[4,5-d]pyrimidin-3(2H)-yl-5-hydroxymethyl tetrahydrofuran-3-yl acetate has certain advantageous properties over the free base, the synthesis of the tosylate salt is challenging. For instance, synthesis requires the use of p-toluenesulfonic acid (TsOH), a known carcinogenic agent. Synthesis of the tosylate salt on a commercial scale is further complicated by the observation that it is accompanied by the formation of genotoxic agents—ethyl-4-methylbenzene sulfonate (ethyl tosylate) and isopropyl-4-methylbenzene sulfonate (isopropyl tosylate) as side products.

Because of the biological toxicity of ethyl tosylate and isopropyl tosylate, time intensive and costly purification methods have to be employed during the commercial-scale manufacture of the tosylate salt. That is, purification protocols capable of removing or reducing the concentrations of the genotoxic byproducts to the single digit parts per million (ppm) ranges required for pharmaceutical formulary use are necessary to obtain a tosylate salt that is suitable for use as a therapeutic agent. In addition to the synthetic challenges, the manufacture of a pharmaceutical composition containing the tosylate salt of 5-amino-2-oxothiazolo[4,5-d]pyrimidin-3(2H)-yl-5-hydroxymethyl tetrahydrofuran-3-yl acetate is challenging.

The inventive co-crystals, synthesized using protocols described below, address several drawbacks and challenges associated with the synthesis and pharmaceutical development of the tosylate salt as a therapeutic for treating HBV and HCV infections. As further described below, the inventive co-crystals are synthesized by contacting 5-amino-2-oxothiazolo[4,5-d]pyrimidin-3(2H)-yl-5-hydroxymethyl tetrahydrofuran-3-yl acetate (Formula I compound) and at least one co-crystal former.

Solvates and salts of the Formula I compound also can form co-crystals when combined with a co-crystal former. To this end, several organic acids have been evaluated as co-crystal formers. Illustrative co-crystal formers include without limitation oxalic acid, L-aspartic acid, maleic acid, saccharin, 2-aminobenzoic acid, L-glutamic acid, L-threonine, 4-aminobenzoic acid, α-ketoglutaric acid, 1-hydroxy-2-naphthoic acid, malonic acid, gentisic acid, salicylic acid, L-(+)-tartaric acid, fumaric acid, galactaric acid, citric acid, D-glucuronic acid, β-cyclodextrin, hydroxypropyl-β-cyclodextrin, 4-aminosalicylic acid, nicotinamide, L(−)-malic acid, hippuric acid, glycolic acid, L(−)pyroglutamic acid, γ-cyclodextrin, benzoic acid, succinic acid, glutaric acid, adipic acid, 4-hydroxybenzoic acid, (+)camphoric acid, sorbic acid, nicotinic acid, orotic acid, urea, methylparabene, propylparabene, L(−)-lactamide, L-ascorbic acid, cinnamic acid, D,L-mandelic acid, vanillic acid and methyl-4-hydroxybenzoate.

In addition to the above mentioned organic acids, the invention also provides for a co-crystal wherein the co-crystal former is a second drug or a second active pharmaceutical ingredient (API). Illustrative of the category "second drug" or "second API" are therapeutic agents comprising antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll receptor-like modulators.

three absorption peaks at 222 nm, 248 nm and 316 nm. In addition, X-ray powder diffraction studies were performed to further characterize the inventive co-crystals. The 2θ values from X-ray powder diffraction studies for several co-crystals in accordance with the invention are listed in Table 2.

TABLE 2

| Co-Crystal Former | Co-Crystal | XRPD 2θ values |
|---|---|---|
| anthranilic acid | Mono Anthranilic acid co-crystals | 8.3, 11.6, 12.4, 14.4, 15.3, 16.5, 18.0, 19.9, 20.4, 20.8, 21.1, 23.6, 26.1, 26.2, 27.0, 27.3, 28.4, 30.3 |
| α-ketoglutaric acid | Mono α-ketoglutaric acid co-crystals | 4.3, 6.0, 6.8, 8.8, 10.1, 11.4, 13.2, 17.8, 18.5, 19.8, 21.3, 21.8, 23.2, 23.7, 23.8, 25.4, 26.4, 26.6, 29.9 |
| Malonic acid | Hemi Malonic acid co-crystal | 3.5, 7.0, 8.8, 10.8, 14.0, 17.4, 17.7, 18.7, 20.3, 22.3, 22.5, 24.3, 24.7, 25.9, 26.7, 29.3, 30.2 |
| Fumaric acid | Hemi Fumaric acid co-crystal | 6.6, 7.3, 8.4, 9.7, 11.0, 12.9, 13.3, 18.1, 19.5, 20.5, 21.5, 22.2, 22.4, 22.7, 23.4, 23.5, 23.9, 24.2, 25.9 |
| Glutaric acid | Hemi Glutaric acid co-crystal | 5.9, 8.1, 11.3, 11.9, 12.4, 15.7, 17.8, 18.3, 18.9, 20.6, 20.8, 21.6, 22.4, 24.2, 24.6, 25.4, 25.6, 26.5, 28.6 |
| Adipic acid | Hemi Adipic acid co-crystal | 7.8, 10.8, 11.9, 12.8, 15.5, 17.9, 18.0, 18.6, 20.6, 21.2, 21.5, 22.1, 24.4, 25.1, 25.6, 26.5, 29.0, 30.4 |

Table 1 illustrates physical characteristics of exemplary co-crystals comprising a Formula I compound and an organic acid co-crystal former in accordance with the present invention. As illustrated in Table 1 and further described below, many of the exemplified co-crystals have superior aqueous solubility permitting their designation as Class I drugs based on the Biopharmaceutics Regulatory Systems (BCS) classification system.

TABLE 1

| Co-Crystal Former | Hygroscopicity | Physical Characteristics | BCS Class |
|---|---|---|---|
| 2-aminobenzoic acid | slightly hygroscopic (±1.8%-m/m) | m.p. 116.3° C. (85.4 J/g) Formula I/co-crystal former ratio 1:1 with acid | — |
| α-ketoglutaric acid | slightly hygroscopic (±0.8%-m/m) | m.p. 135.5° C. (116.7 J/g) Formula I/co-crystal former ratio 1:1 with acid | — |
| Malonic acid | slightly hygroscopic (±0.3%-m/m) | m.p. 140.3° C. Formula I/co-crystal former ratio 1:0.5 with acid | 2 |
| Fumaric acid | 1st cocrystal slightly hygroscopic (±0.6%-m/m) | m.p. 157.3° C., Formula I/co-crystal former ratio 1:0.5 with acid | 1 |
| Glutaric acid | slightly hygroscopic (±0.3%-m/m) | m.p. 148.4° C. (106.8 J/g) Formula I-co-crystal former ratio 1:0.5 with acid | 1 |
| Adipic acid | slightly hygroscopic (±0.3%-m/m) | m.p. 127.3° C. (97.7 J/g) Formula I-co-crystal former ratio 1:0.5 with acid | 1 |

The inventive co-crystals were further characterized using X-ray powder diffraction (XRPD) spectroscopy, nuclear magnetic resonance (NMR) spectroscopy, light microscopy and infrared (IR) spectroscopy. Thus, polarized light microscopy of a suspension of glutaric acid co-crystals in paraffin oil indicated a crystalline solid. Solid state NMR studies confirm Formula I glutaric acid co-crystals while solution phase NMR studies confirm a 2:1, Formula I compound to glutaric acid (co-crystal former) stoichiometry for a co-crystal in accordance with the present technology. UV-spectrophotometric studies of an ethanol solution of an exemplary glutaric acid co-crystal (0.27 mg/mL), showed To the surprise of the present inventors co-crystals in accordance with the present invention have several advantages compared to the tosylate salt of a Formula I compound. For instance, synthesis of co-crystals using the synthetic protocol described below is less time-consuming. The inventive synthetic methodology is readily amenable to scale-up, permitting the commercial synthesis and isolation of the co-crystals. Purification of the inventive co-crystals is cost-effective and quick. Simple filtration and washing is sufficient to obtain co-crystals that are suitable for use as pharmaceutical agents. The synthesis of co-crystals in accordance with this invention, moreover, eliminates the production of genotoxic side-products that accompanied the manufacture of the tosylate salt.

In addition to the above mentioned advantages, the inventive co-crystals have enhanced chemical stability and are less sensitive to degradation by hydrolysis than the amorphous free base or the tosylate salt of 5-amino-2-oxothiazolo[4,5-d]pyrimidin-3(2H)-yl-5-hydroxymethyl tetrahydrofuran-3-yl acetate. Thus, while the inventive co-crystals can be stored at room temperature for an extended period of time, the corresponding p-toluenesulfonic acid salt is hygroscopic and requires storage at cold temperatures to prevent degradation.

Another advantage is that co-crystals in accordance with the present invention have a very low amount of residual solvent. This permits the manufacture of pharmaceutical compositions of the inventive co-crystals with very low amounts, if any, of residual solvent. In addition, solubility studies suggest the inventive co-crystals to be highly soluble in water which is desirable for the manufacture of pharmaceutical compositions. Because of their high aqueous solubility, the co-crystals are classified as Class I drugs, in accordance with the Biopharmaceutics Regulatory Systems (BCS) guidelines.

The salt factor (S), which refers to the fraction of the administered dose of a drug that is in the form of a salt or an ester influences pharmacokinetics and bio-distribution. For instance, the salt factor (S) influences amongst other factors the plasma concentration of a drug, the dose required to attain a steady state concentration of the API in plasma, the bio-availability of the API and bio-distribution of drugs. To the surprise of the present inventors, co-crystals of the Formula I compound have lower value for "S" (the pharmaceutical salt factor) than the corresponding tosylate salt of the Formula I compound. For instance, the salt factor (S) for an exemplary glutaric acid co-crystal is 1.2. The salt factor (S) for the tosylate salt of the Formula I compound (5-amino-2-oxothiazolo[4,5-d]pyrimidin-3(2H)-yl-5-hydroxymethyl tetrahydrofuran-3-yl acetate) is greater, about 1.53. Thus, each gram of the glutaric co-crystal contains a greater amount of 5-amino-2-oxothiazolo[4,5-d]pyrimidin-3(2H)-yl-5-hydroxymethyl tetrahydrofuran-3-yl acetate free base compared to a gram of the corresponding tosylate salt.

Stated differently, a pharmaceutical composition comprising glutaric acid co-crystals will contain a greater amount of 5-amino-2-oxothiazolo[4,5-d]pyrimidin-3(2H)-yl-5-hydroxymethyl tetrahydrofuran-3-yl acetate free base in each unit dose. Consequently, fewer doses of the pharmaceutical composition of the co-crystal need to be administered to a patient each day, which can be advantageous for increasing patient compliance during therapy.

For illustrative purposes only, let the daily dose of 5-amino-2-oxothiazolo[4,5-d]pyrimidin-3(2H)-yl-5-hydroxymethyl tetrahydrofuran-3-yl acetate free base be about 1600 mg/day. If an oral formulation (tablet) is manufactured such that the maximum weight of each tablet cannot exceed 1000 mg, and the maximum amount of 5-amino-2-oxothiazolo[4,5-d]pyrimidin-3(2H)-yl-5-hydroxymethyl tetrahydrofuran-3-yl acetate free base that can be present in each tablet cannot exceed 70% by weight of the tablet, then the total number of tablets that need to be administered to a patient to attain the targeted daily dose of 1600 mg free base will depend on (A) the specific form of the Formula I compound used in the manufacture of the tablet and (B) the salt factor (S) associated with the specific form of the Formula I compound.

As illustrated in Table 3, the salt factor(S) of the specific form of the Formula I compound influences the number of tablets needed to achieve the target daily dose of 1600 mg free base. Fewer tablets are needed to achieve the target daily dose when the oral formulation comprises the free base or the glutararte co-crystal of a Formula I compound. If the total weight of a tablet comprising the free base of a Formula I compound is 770 mg (salt factor (S) of the free base is 1.0), each tablet will contain 539 mg of the free base (0.7×770 mg). Because the free base is difficult to synthesize and purify on a commercial scale and as mentioned above tablets comprising the free base suffer from poor stability and short shelf life, a tablet formulation of the free base is unsuitable for commercialization.

In comparison, four tablets of the tosylate salt are needed to attain the target daily dose of 1600 mg of the free base of a Formula I compound. For example, if the weight (mg) per unit dose, that is, the weight of a tablet containing the tosylate salt of a Formula I compound is 875 mg and the salt factor (5) is 1.53, each 875 mg tablet will contain 612.5 mg (70% of the total weight of the tablet) of the tosylate salt which corresponds to 400 mg (612.5/1.53) of the corresponding free base per tablet. Four tablets of the tosylate salt, therefore, need to be administered to a patient to achieve the targeted daily dose of 1600 mg free base. Thus, not only will a patient need to orally ingest more tablets if the tosylate salt is used as the drug, but such a patient will need to swallow a much larger tablet which can be challenging for children and aged patients in need of therapy.

The lower value of the salt factor for the inventive co-crystals compared to the tosylate salt reduces the number of tablets containing the co-crystal that are needed on a daily basis. For instance, if a tablet containing the glutaric acid co-crystal weighs 930 mg, such a tablet will contain 612.5 mg (70% of 930 mg) by weight of the glutaric acid co-crystal. The amount of free base in each tablet, therefore, is 533.7 mg (612.5/1.22). It is clear from the above discussion that a tablet containing glutaric acid co-crystals contains a greater amount of the free base (i.e., weight of free base in mg/unit dose) compared to a tablet containing the corresponding tosylate salt. Thus, fewer tablets of the co-crystal are needed to attain the targeted daily dose of 1600 mg as illustrated in Table 3.

TABLE 3

|  | Free Base (Formula I) | Tosylate Salt | Co-crystal with Glutaric Acid |
|---|---|---|---|
| M.W. (g/mol) | 326 | 498 | 392 |
| Salt factor | 1.0 | 1.53 | 1.2 |
| Weight of tablet in mg/unit dose | 770 | 875 | 930 |
| No. of tablets | 3 | 4 | 3 |
| Total weight of all tablets/day (mg) | 2310 | 3500 | 2790 |

Pharmaceutical Compositions and Dosages

The present invention also is directed to pharmaceutical formulations of the inventive co-crystals and the use of such pharmaceutical formulations for the treatment of disease conditions such as cancer, viral infections, or diseases associated with improper immune function. In one aspect, therefore, the present invention relates to a pharmaceutical formulation of co-crystal comprising a Formula I compound or a pharmaceutically acceptable stereoisomer, tautomer, or solvate and at least one co-crystal former as well as pharmaceutically acceptable excipients.

The inventive compositions may further contain in accordance with accepted practices of pharmaceutical compounding, one or more additional therapeutic agents, pharmaceutically acceptable diluents, adjuvants, stabilizers, emulsifiers, preservatives, colorants, buffers, or flavor imparting agents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Pharmaceutical compositions suitable for single unit dosages that comprise a co-crystal of the invention and a pharmaceutically acceptable carrier are also encompassed within the scope of the present disclosure. Pharmaceutical formulations as well as single unit dosage forms according to the present invention may be suitable for oral, mucosal (including sublingual, buccal, rectal, nasal, or vaginal), parenteral (including subcutaneous, intramuscular, bolus injection, intra-arterial, or intravenous), transdermal, or topical administration. Sterile formulations of the inventive co-crystal are also contemplated.

Pharmaceutical formulations as well as single unit dosage forms can contain various amounts of the co-crystal, its pharmaceutically acceptable salt or tautomer. For instance, the amount of co-crystal in the pharmaceutical formulations as well as single unit dosage forms may range from about 0.1 mg to about 1000 mg. For some formulations and single dosage forms the amount of co-crystal is from about 50 mg to about 750 mg, from about 50 mg to about 500 mg, from about 100 mg to about 250 mg, from about 10 mg to about 100 mg, or about 1 mg to about 10 mg.

Anhydrous pharmaceutical compositions comprising a co-crystal of the invention also are encompassed within the scope of this disclosure. Since moisture and/or humidity are routinely encountered during the manufacture, storage, handling, packaging, shipment and use of pharmaceutical formulations, methods for preparing anhydrous pharmaceutical compositions and dosage forms of the disclosure using anhydrous or low moisture containing ingredients and low moisture or low humidity conditions known to those skilled in the formulations art are within the scope of this disclosure.

To maintain the anhydrous nature of a pharmaceutical composition of the co-crystals, the inventive pharmaceutical formulations should be packaged and stored under conditions that maintain its anhydrous nature. Accordingly, anhydrous compositions are preferably packaged using materials known to prevent exposure to water. Examples of suitable packaging include, but are not limited to, hermetically sealed foils, plastics, unit dose containers (e.g., vials), blister packs, and strip packs.

Co-crystals in accordance with the present invention are therapeutics for the treatment of diseases or disorders associated with improper cell division, improper immune function, or to treat viral infections. Treatment may be effected by administering one or more therapeutically effective doses of the inventive co-crystals to a patient or subject in need of treatment.

Oral Dosage Forms

Inventive compositions suitable for oral use may be prepared according to any method known in the art for the manufacture of pharmaceutical compositions. See generally, *Remington's Pharmaceutical Sciences*, 18th ed., Mack Publishing, Easton Pa. (1990). Such oral dosage forms contain predetermined amounts of active ingredients in an intimate admixture with at least one excipient. Liquid formulations can further contain sweetening agents, flavoring agents, coloring agents and preserving agents in order to provide pharmaceutically elegant and palatable preparations of a co-crystal of the invention.

Suitable oral compositions in accordance with the invention include without limitation tablets, troches, lozenges, aqueous or oily suspensions, dispersible powders or granules, emulsion, hard or soft capsules, syrups or elixirs. Because of their ease of administration, storage and packaging, tablets and capsules represent the most advantageous oral dosage unit forms, in which case solid excipients are employed. If desired, tablets can be coated by standard aqueous or nonaqueous techniques. In general, pharmaceutical compositions and dosage forms are prepared by uniformly and intimately admixing the active ingredients, namely the co-crystal, with liquid carriers, finely divided solid carriers, or both, and then shaping the product into the desired presentation if necessary.

For tablet compositions the active ingredient in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin, gums such as acacia, and lubricating agents, for example magnesium stearate, stearic acid or talc. The binder or filler used for a pharmaceutical composition of the invention is typically present in from about 50 to about 99 weight percent of the pharmaceutical composition or dosage form.

Tablets can be prepared by compression or molding and may be uncoated or coated to delay disintegration and absorption in the gastrointestinal tract and thereby to provide a sustained therapeutic action over a desired time period. Exemplary time delay materials include without limitation glyceryl monostearate or glyceryl distearate.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

In addition to tablets and capsules, a co-crystal of the invention may be formulated as syrups, suspensions, dispersible powders and granules that are suitable for oral administration. When formulated as an oral suspension, the pharmaceutical composition can contain dispersing or wetting agents, such as naturally-occurring phosphatide, for example, lecithin, or condensation products of an alkylene oxide with a fatty acid, a long chain aliphatic alcohol, or partial esters of fatty acids. Illustrative of such products are polyoxyethylene stearate, heptadecaethyleneoxycetanol, a hexitol such as polyoxyethylene sorbitol monooleate, or polyethylene sorbitan monooleate. Oral suspensions may also contain one or more preservatives, for example ethyl or n-propyl p-hydroxybenzoate, one or more coloring agents, one or more flavoring agents, and one or more sweetening agents, such as sucrose or saccharin. Syrups and elixirs may be formulated with sweetening agents, for example glycerol, propylene glycol, sorbitol or sucrose. Such formulations may also contain a demulcent, a preservative, and flavoring and coloring agents.

Delayed Release Dosage Forms

The inventive co-crystals can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations are known to those of ordinary skill in the formulary art. The disclosure thus encompasses single unit dosage forms suitable for oral administration such as, but not limited to, tablets, capsules, gel caps, and caplets that are adapted for controlled-release.

All controlled-release pharmaceutical products have a common goal of improving drug therapy over that achieved by their non-controlled counterparts. Ideally, the use of a controlled-release preparation in medical treatment is characterized by administration of a known quantity of the active agent over a pre-determined time interval, such as a 2 days, 3, days, 4 days, 5 days, 6 days, 1 week, 2 weeks, 3 weeks, 4 weeks, or from 2-12 months, 3-12 months, 4-12 months, 5-12 months, 6-12 months, 7-12 months, 8-12 months, 9-12 months, 10-12 months, 11-12 months, or 1 year. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release the same or other amounts of drug to maintain the same levels of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial injections. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the disclosure are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Parenteral formulations can include compounds that increase the solubility of one or more of the active pharmaceutical ingredients or an inventive co-crystal in accordance with the invention.

Kits

The disclosure provides a pharmaceutical pack or kit comprising one or more containers comprising a co-crystal in accordance with the invention and can optionally include one or more containers containing a pharmaceutically acceptable carrier. In other embodiments, the disclosure provides a pharmaceutical pack or kit comprising one or more containers comprising a co-crystal in accordance with the invention, one or more containers comprising an additional therapeutic agent and one or more containers containing a pharmaceutically acceptable carrier.

A kit or a pack in accordance with the invention may comprise one or more containers or packets comprising one or more of the pharmaceutical ingredients necessary for formulating the inventive co-crystal into a pharmaceutical composition suitable for administration as well as devices such as one or more syringes for administering a pharmaceutical composition of the inventive co-crystal.

Kits or packs may include buffers, compounds to adjust the tonicity of the pharmaceutical carrier and compounds to alter the hydrophilic-lipophilic balance (HLB) so as to improve delivery and bio-distribution. Optionally associated with the container(s) present in a kit or a pack can be a notice in the form prescribed by a governmental agency regulating the manufacture, use or sale of pharmaceuticals or biological products, which notice reflects approval by the agency of manufacture, use or sale for human administration.

Combination Therapy

In one aspect, a therapeutically effective dose of a co-crystal of the invention may be administered along with a therapeutically effective dose of the combination drug (additional therapeutic agent) to a patient or subject in need of treatment. The person of skill in the art will recognize that a dose of the co-crystal may be administered separately, say within seconds, minutes or hours before or after the administration of the combination drug or the two doses may be administered together. The additional therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, pegylated α-interferon, pegylated β-interferon, ribavirin, alkylating agents, hormones, cytokines, or toll receptor-like modulators.

In addition to the above therapeutic agents, the present invention encompasses combination therapy regimens that include a co-crystal in combination with a therapeutically effective amount of a polymerase inhibitor, for example, lamivudine, adefovir, entecavir and telbivudine. Therapeutic regimens comprising the combination of three drugs are also encompassed within the scope of the invention. For instance, such a regimen can encompass the administration of therapeutically effective doses of the co-crystal, a polymerase inhibitor and an interferon or a pegylated interferon.

The percentages of each compound or a pharmaceutically acceptable salt or tautomer thereof, present in a composition can also vary. For example, in some embodiments, the composition can include an amount of the co-crystal or a pharmaceutically acceptable salt or tautomer in the range of about 1% to about 98% (weight/weight). The composition can contain the inventive co-crystal or a pharmaceutically acceptable salt or tautomer thereof, in the range of about 5% to about 80%, about 10% to about 70%, about 15% to about 60%, about 20% to about 50% and about 30% to about 40% (weight/weight).

When an antibiotic is used as the second therapeutic agent, illustrative compounds include without limitation, macrolides (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The inventive co-crystal can be administered or formulated in combination with other antiviral agents too. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, didanosine, stavudine, combivir, abacavir, adefovir, dipivoxil, cidofovir, ribavirin and its analogs, levovirin, viramidine, isatoribine, pirfenidone, or its analogs, acyclovir, gangcyclovir, vidarabine, idoxuridine, trifluridine, and as well as foscarnet, amantadine, rimantadine, saquinavir, indinavir, amprenavir, lopinavir, ritonavir, the α-interferons; β-interferons; clevadine, entecavir, pleconaril.

Additional therapeutic agents can include tumor necrosis factor antagonists, such as etanercept, infliximab and adalimumab), thymosin-.alpha. (Zadaxin.™.), an interferon receptor agonist(s), α-glucosidase inhibitors, TNF-α antagonists, NS3 helicase inhibitors, inhibitors of NS5B polymerase (such as GS-9190, MK-3281, VCH-759 (VX-759), VCH-916, ABT-333, BMS-791325, PF-00868554, IDX-184, R1626, PSI-7851, VCH-222 (VX-222), ABT-072, and BI207127) and inhibitors of the NS5A protein (such as BMS-790052, A-831, and AZD2836).

The inventive co-crystal can be administered or formulated in combination with an agent which inhibits viral NS3 protease, for example, VX-950 and SCH 503034, toll-like receptor (TLR) modulators such as IMO-2125, and PF-04878691; cytochrome P450 monooxygenase inhibitors; ribozymes such as Heptazyme™ and phosphorothioate oligonucleotides, which are complementary to HBV protein sequences and which inhibit the expression of viral core proteins.

Alternatively, a co-crystal of the present invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll receptor-like (TLR) modulators. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

When administered in combination with an additional therapeutic agent, the co-crystal and the other therapeutic agent can act additively or, more preferably, synergistically. In one embodiment, a composition comprising a co-crystal of the disclosure is administered concurrently with the administration of another therapeutic agent, which can be part of the same composition or in a different composition from that comprising the compounds of the disclosure. In another embodiment, the co-crystal may be administered prior to or subsequent to administration of another therapeutic agent. In a separate embodiment, a co-crystal of the disclosure is administered to a patient who has not previously undergone or is not currently undergoing treatment with another therapeutic agent, particularly an antiviral agent.

EXAMPLES

I. Compatibility Studies

Compatibility of the inventive co-crystals with pharmaceutically acceptable excipients was determined by the classic compatibility assay (COMPASS). According to this method, excipient compatibility was investigated by physically mixing the inventive glutaric acid co-crystals with a single pharmaceutical excipient so as to form a binary mixture or by physically mixing the inventive glutaric acid co-crystals with mixtures containing two or more excipients (ternary mixture). Each binary mixture contained 5% by weight of the Formula I compound, whereas the weight percent of the Formula I compound in a ternary mixture was 50%. The test mixtures were stored at 50° C. for 4 weeks or at a temperature of 40° C. and a relative humidity of 75% for 4 weeks.

The inventive co-crystals are compatible with fillers and/or excipients commonly used in the manufacture of pharmaceutical compositions. Table 4 illustrates the results of a compatibility study using ternary mixtures of the inventive glutaric acid co-crystal of the Formula I compound. Table 5 illustrates the results for a similar study using ternary mixtures of the tosylate salt of the Formula I compound.

acceptable formulations. The corresponding tosylate salt, however, was found to be unstable with commonly used excipients and/or fillers.

TABLE 4

| Glutaric acid co-crystal | Reference 4 weeks at 2-8° C. % area Formula I | 4 weeks at 50° C. | | | 4 weeks at 40° C./75% RH | | |
|---|---|---|---|---|---|---|---|
| | | % area Formula I | % degradation | Stability | % area Formula I | % degradation | Stability |
| Ternary mixture 1 | 99.775 | 99.810 | −0.035 | Fairly stable | 99.730 | 0.045 | Fairly stable |
| Ternary mixture 2 | 99.745 | 99.723 | 0.023 | Fairly stable | 99.725 | 0.020 | Fairly stable |
| Ternary mixture 3 | 99.810 | 99.713 | 0.098 | Fairly stable | 99.720 | 0.090 | Fairly stable |
| Control crystalline Formula I | 99.710 | 99.670 | 0.040 | Fairly stable | 99.740 | −0.030 | Fairly stable |

TABLE 5

| Tosylate salt | 4 weeks/50° C. | | | 4 weeks/40° C./RH 75% | | |
|---|---|---|---|---|---|---|
| | % area (Formula I) | % degradation | Stability | % area (Formula I) | % degradation | Stability |
| Ternary mixture 1 | 98.74 | 0.54 | | 98.01 | 1.31 | unstable |
| Ternary mixture 2 | 98.96 | 0.23 | Fairly stable | 90.12 | 9.25 | unstable |
| Ternary mixture 3 | 99.03 | 0.16 | Fairly stable | 93.91 | 5.44 | unstable |
| Control crystalline (Formula I) | 99.19 | — | | 99.31 | — | |

Ternary mixtures comprising the inventive glutaric acid co-crystal or the tosylate salt of a Formula I compound contained the following excipients in proportions illustrated in Table 6 below.

TABLE 6

| Excipient | Ternary Mixture 1 % | Ternary Mixture 2 % | Ternary Mixture 3 % |
|---|---|---|---|
| Mannitol | 40 | | |
| Lactose monohydrate | | 40 | |
| HPMC | 16.01 | | |
| Maltodextrin | | | 40 |
| Microcrystalline cellulose | 33.99 | 30 | |
| Starch 1500 | | | 31.99 |
| Croscarmellose sodium | 6.01 | | |
| Sodium starch glycolate | | | 6.01 |
| PVP K30 | | 16.01 | 16.01 |
| Crospovidone | | 6.01 | |
| Sodium stearyl fumarate | 3.99 | | |
| Magnesium stearate | | 3.99 | 3.99 |
| Talc | | 3.99 | |
| Aerosil 200 | | | 1.99 |

The results from the compatibility studies, Tables 4 and 5 clearly show the inventive glutaric acid co-crystals to be more compatible with pharmaceutical excipients and fillers commonly used during the manufacture of pharmaceutically acceptable formulations. The corresponding tosylate salt, however, was found to be unstable with commonly used excipients and/or fillers.

For instance, storage of ternary mixtures comprising glutaric acid co-crystals and a pharmaceutical fillers or excipients for 4 weeks at 50° C. or for 4 weeks at 40° C./75% relative humidity showed very little degradation of the Formula I compound. Typical ranges for percent degradation were from about 0.02% to 0.098% at 50° C. The presence of humidity does not adversely impact the compatibility and/or stability of ternary mixtures the inventive co-crystal, there was no increase in the percent degradation of the Formula I compound at 40° C. and in the presence of 75% relative humidity.

In contrast, the percent degradation of the Formula I compound in ternary mixtures comprising the tosylate salt of a Formula I compound and two or more pharmaceutical fillers or excipients was greater. It is evident that the presence of moisture compromised the compatibility of ternary mixtures containing the tosylate salt. As illustrated in Table 5, the presence of humidity increases degradation of the ternary mixtures. For the tosylate salt, ternary mixture 2 showed about 10% degradation in the presence of humidity compared to 0.02% degradation for a similar ternary mixture of the inventive glutaric acid co-crystal.

These data clearly illustrate that the inventive glutaric acid co-crystals are more compatible than the tosylate salt with excipients and fillers used commonly in the manufacture of pharmaceutical formulations.

II. Stability Studies

Solid state stability studies were performed by storing a test sample of the co-crystal at different temperatures and under conditions of different relative humidity for a period of one to three months. Stability was judged by Ultra performance liquid chromatography (UPLC) analysis of the test co-crystals. Percent degradation of API in a test sample of the co-crystal was calculated as follows:

$$\% \text{ Degradation} = \frac{\% \text{ AUC for API of reference sample} - \% \text{ AUC for API of test sample}}{\% \text{ AUC for API of reference sample}} * 100$$

Co-crystals in accordance with the invention are fairly stable across the temperature range used in the study. Storage in the presence of humidity (75% relative humidity (R.H.)) did not increase the percent degradation of the inventive co-crystals. Without ascribing to a particular theory, crystallinity may contribute to the stability of inventive co-crystals. Table 7 illustrates data from a stability of a Formula I glutaric acid co-crystal in accordance with the invention across a range of temperatures and in the presence of 75% relative humidity at 40° C.

TABLE 7

| Storage conditions | T0 % Area Formula I | 1 month | | 2 months | |
|---|---|---|---|---|---|
| | | % Area Formula I | % degradation | % Area Formula I | % degradation |
| Formula I compound | 98.94* | — | | | |
| 2-8° C. | — | 99.02 | −0.08 | 99.32** | |
| RT | — | 98.9 | 0.04 | 99.22 | −0.10 |
| 40° C. | — | 99.05 | −0.11 | 99.35 | −0.04 |
| 40° C./75% r.h. | — | 99.14 | −0.2 | 99.34 | −0.03 |
| 60° C. | — | 99.01 | −0.07 | 99.56 | −0.25 |

*used as reference for 1 month stability;
**used as reference for 2 month stability As illustrated in Table 7, the glutarate co-crystal of a Formula I compound shows superior stability over a wide range of storage temperatures and in the presence of humidity. Further supporting the hypothesis that crystallinity contributes to increased stability was provided by comparing the amorphous form of the free base of a Formula I compound to the crystalline form of a Formula I compound as illustrated in Table 8.

TABLE 8

| | T0 % Area Formula I | 4 weeks/40° C./ ambient conditions (closed container) | | 4 weeks/ 40° C./75% r.h. | |
|---|---|---|---|---|---|
| | | % Area Formula I | % degradation | % Area Formula I | % degradation |
| free base Formula I-crystalline | 99.71 | 99.52 | 0.19 (stable) | 99.56 | 0.15 (stable) |
| free base Formula I-amorphous | 99.90 | 98.89 | 1.011 (moderately stable) | 86.34 | 13.57 (very unstable) |

The above results suggest that crystallinity does have a major impact on stability since the crystalline form is more stable to degradation than the corresponding amorphous form, especially in the presence of moisture. Thus, crystallinity also may be contributing to the improved stability of the inventive co-crystals.

The improved stability of the inventive co-crystals has certain advantages. Greater stability may permit better handling and ease of use of the co-crystals, especially during the commercial scale manufacture of the co-crystals and the commercial scale manufacture of pharmaceutical formulations of co-crystals. Enhanced stability may also contribute to increasing the shelf life of solid pharmaceutical compositions, such as tablets containing the co-crystals.

Because the crystalline form is not retained in solution, that is when a co-crystal is dissolved in a solvent, only interactions between the Formula I compound and the solvent play a role in influencing the solution stability. Accordingly, solutions of the co-crystal, the tosylate salt or the crystalline form of the free base are expected to show comparable solution stabilities under the same experimental conditions.

III. Development of Formulations for Pharmacokinetics & Toxicological Studies of the Co-Crystals Studies have shown that the co-crystals were soluble in water and buffered solvents. These studies revealed that pH of the solvent influences the solubility of the co-crystals. Solubility was greatest at low pH, for example, in buffer at a pH of 1.0 or a pH of 2.0, and the solubility decreased as the pH of the buffer increased. UPLC analysis of a pH 1.0 buffered solution of glutaric acid co-crystal indicates that greater than 60 mg of the free-base form of the Formula I compound is present per milliliter of the buffer solution. However, a significantly lesser amount, about 22 mg of the free-base form of the Formula I compound is present per milliliter of a pH 7.0 buffered solution based on UPLC analysis. Interestingly, solubility was lowest in a pH 4.0 buffer, about 8 mg of the free base form is present per milliliter of the buffer, most likely due to the formation of the zwitterionic form of the Formula I compound.

Analysis of the buffered co-crystal solutions after 24 hours incubation at room temperature showed no degradation. Unlike the tosylate salt, no genotoxic by-products are formed in solutions of the inventive co-crystals. Polymorph screening further showed a single polymorph for an exemplary glutaric acid co-crystal which was characterized as solid state Form A.

A. Pharmacokinetics

Studies were undertaken to compare the pharmacokinetics (PK) of the glutaric acid co-crystal to the PK of the tosylate salt of the Formula I compound. A 3% solution of Blanose 7LF PM without preservatives was used to formulate the glutaric acid co-crystal and tosylate salt. Results from a pharmacokinetic study in cynomolgus monkeys indicate that the plasma concentration of the glutaric acid co-crystal was greater than the corresponding tosylate salt following oral administration of each compound.

In this study, each compound was administered orally at a dose of 10 mg/kg to cynomolgus monkeys. Following administration, blood was obtained from each test subject at 0 min, 60 min, 120 min and 180 minutes. After separating the plasma from whole blood an aliquot to each plasma sample was denature by the addition of 70% ethanol. The denatured protein was pelleted by centrifugation and the supernatant was collected and dried using a stream of dry nitrogen gas. The pellet thus obtained was re-constituted in water containing 0.1% formic acid and the re-constituted mixture was analyzed by UPLC using a HSS-T3 (high strength silica) column or an YMC TriartC-18 column. Gradient elution using a mixture of water containing 0.1% HCOOH (mobile phase-A) and acetonitrile containing 0.1% HCOOH (mobile phase-B) was employed for analysis of the pharmacokinetic (PK) samples.

As shown in FIG. 1, oral administration of the glutaric acid co-crystal provided a higher concentration of the co-crystal in circulating plasma. In fact, the detected plasma concentration of the de-acetylated form of the Formula I compound following oral administration of the glutaric acid co-crystal is about two-fold greater compared to the detected plasma concentration of the de-acetylated form of the Formula I compound following oral administration of the tosylate salt.

The higher concentration of the de-acetylated form of the Formula I compound following oral administration of the co-crystal results in higher levels of the active pharmaceutical species too, namely, the de-acetylated, oxidized form of the Formula I compound. See Scheme 1. The compound of Formula I is a double pro-drug which is enzymatically converted to the biologically active pharmaceutical agent 5-amino-3-((2R,3R,5S)-3-hydroxy-5-(hydroxymethyl)tetrahydrofuran-2-yl)-3a,7a-dihydrothiazolo[4,5-d]pyrimidine-2,7(3H,6H)-dione as shown in Scheme 1 below.

B. Oral GLP Toxicological Studies

Three vehicles, Blanose 7LF PM (sodium carboxymethyl cellulose) without preservative, Pluronic F60, and plyvinyl alcohol, were tested as pharmaceutical carriers for the inventive co-crystals. Because the co-crystals showed good aqueous solubility, surfactants were not be added to the pharmaceutical formulations containing co-crystals.

Toxicological studies were carried out using formulations containing different amounts (concentrations) of the inventive co-crystals. Briefly, known amounts of a glutaric acid co-crystal were dissolved in each carrier so as to provide formulations containing 100 mg/mL, 10 mg/mL, and 1 mg/mL of the free base (Formula I compound). Each test formulation was split into three equal parts and stored at room temperature, 2-8° C. and −20° C. Following storage for seven days, each formulation was analyzed for content and purity by Ultra Performance Liquid Chromatography Scheme 1

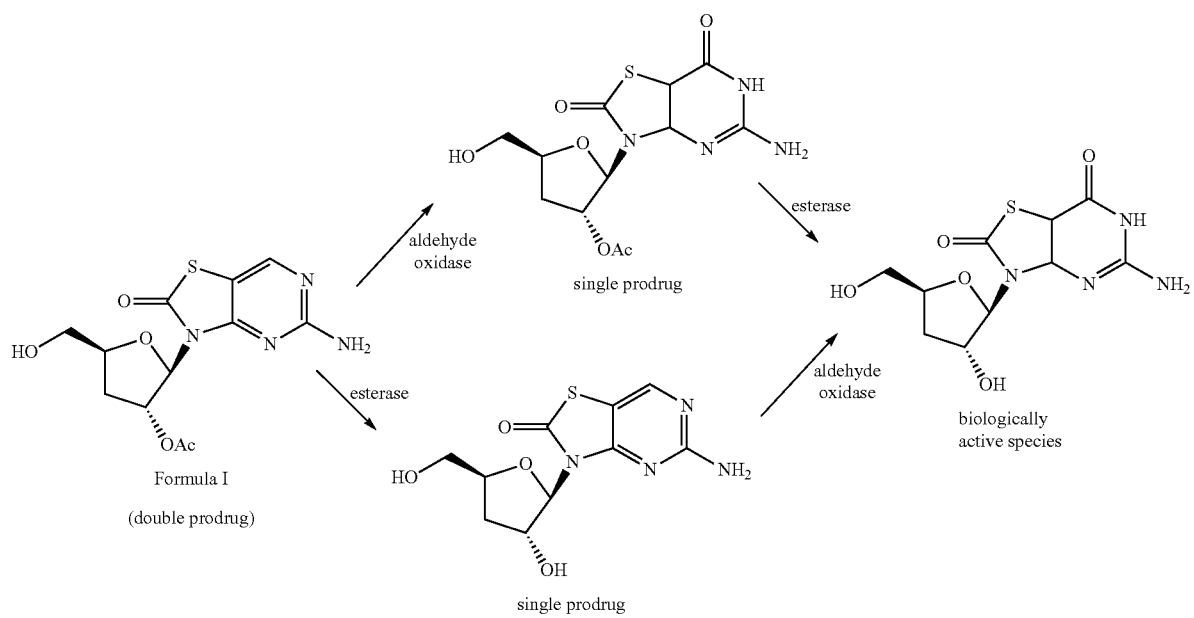

In contrast, lower levels of the de-acetylated form of the Formula I compound and biologically active species are observed in plasma obtained from monkeys dosed with the corresponding tosylate salt at an oral dose of 10 mg/kg. Several factors may account for the observed differences in the concentration of pro-drug and active species in plasma. Without being bound to a particular theory, one hypothesis is that the greater stability of the co-crystal, the greater solubility of the co-crystals in biological medium and a lower rate of clearance of the co-crystal by the liver and kidneys compared to the corresponding tosylate salt may contribute to the observed higher plasma levels of the de-acetylated and active species following oral administration of a formulation of the glutaric acid co-crystals.

Based on the PK results the inventive co-crystals are considered to be better candidate therapeutics for the development of therapies targeting cancer, viral infection including HBV infection.

(UPLC) and for particle size by light microscopy. The pH of each formulation was also measured.

pH of the formulations were not affected by the carriers and remained the same over the seven day test period. Depending on the carrier used, measured pH values were in the range from 4.0 to 5.6 for test formulations at all storage temperatures. While some amount of degradation was observed in all the test formulations, the percent degradation was within a pharmaceutically acceptable range. However, the formulation containing Blanose 7LF PM showed the greatest percent degradation compared to formulations made using the other two carriers.

As Table 9 illustrates de-acetylation of the double prodrug (Formula I compound glutaric acid co-crystal) to the single prodrug (unacetylated) form of Formula I compound was observed in many of the test formulations.

TABLE 9

| | | 100 mg/mL free base | | | 10 mg/mL free base | | | 1.0 mg/mL free base | | |
|---|---|---|---|---|---|---|---|---|---|---|
| Vehicle | Storage Time/ condition | Measured [mg/mL] Formula I | Purity [area %] | De-acetylated [area %] | Measured [mg/mL] Formula I | Purity [area %] | De-acetylated [area %] | Measured [mg/mL] Formula I | Purity [area %] | De-acetylated [area %] |
| 3% Blanose 7LF PM | T0 | 101.8 | 99.99 | — | 10.6 | 100.00 | — | 1.08 | 100.00 | — |
| | 1 w/ RT | 107.9 | 99.82 | — | 11.2 | 99.35 | 0.54 | 1.06 | 97.02 | 3.1 |
| | 1 w/ 2-8° C. | 105.3 | 99.82 | — | 10.8 | 99.68 | 0.18 | 1.12 | 99.53 | 0.1 |
| | 1 w/ −20° C. | 109.1 | 99.86 | — | 10.5 | 99.87 | — | 1.09 | 99.70 | — |
| 10% pluronic F60 | T0 | 107.7 | 100.00 | — | 11.1 | 100.00 | — | 1.09 | 100.00 | — |
| | 1 w/ RT | 109.6 | 99.88 | — | 11.0 | 99.54 | 0.16 | 1.10 | 99.58 | 0.16 |
| | 1 w/ 2-8° C. | 110.1 | 99.87 | — | 11.5 | 99.79 | — | 1.08 | 99.60 | — |
| | 1 w/ −20° C. | 105.5 | 99.86 | — | 11.2 | 99.82 | — | 1.10 | 99.65 | — |
| 2% PVA | T0 | 105.6 | 100.00 | — | 10.4 | 100.00 | — | 1.00 | 100.00 | — |
| | 1 w/ RT | 108.1 | 99.89 | — | 9.84 | 99.59 | 0.23 | 1.01 | 99.48 | 0.18 |
| | 1 w/ 2-8° C. | 108.3 | 99.87 | — | 9.96 | 99.75 | 0.12 | 1.03 | 99.72 | — |
| | 1 w/ −20° C. | 108.9 | 99.94 | — | 9.81 | 99.81 | — | 1.02 | 99.55 | — |

De-acetylation was most pronounced in the Blanose 7LF PM formulation and least present in the Pluronic F60 formulation. These results indicate that the nature of the carrier can influence the rate and extent of degradation of the active pharmaceutical, the extent of sedimentation observed, and the formation of a solid cake-like material following storage.

Sedimentation and the formation of a solid cake like product were most pronounced in the PVA and Pluronic F60 formulations. Unlike the sediment formed in the PVA formulation, the sediment formed in the Pluronic F60 formulation could readily be dispersed by shaking. Sediment formation was relatively slow in the Blanose formulation. However, once a solid cake was formed in the Blanose formulation, the solid could not readily be suspended by stirring or shaking.

After one month storage at room temperature, the 10% Pluronic F60 formulation was chosen as the carrier for in vitro and/or in vivo efficacy studies because of its ease of handling, enhanced stability even after prolonged storage.

IV. Methods of Preparation

Co-crystals comprising a Formula I compound and at least one co-crystal former can be synthesized by combining a solution of the co-crystal former with a solution of a Formula I compound. Specifically, the two solutions are combined at a molar ratio of co-crystal former to a Formula I compound that promotes co-crystallization.

According to one embodiment of the inventive methodology, the co-crystal former and a Formula I compound are combined at a molar ratio of 1:2. The co-crystallization solution thus obtained is supersaturated to initiate the formation of co-crystals. Cooling, evaporation of solvent or the addition of anti-solvent may be used to of super saturate the co-crystallization solution and initiate co-crystal formation. The co-crystals comprising a Formula I compound and at least one co-crystal formers may be isolated from the co-crystallization solution by filtration or other suitable methods known in the chemical art.

Since the formation of a co-crystal requires contact between a Formula I compound and a co-crystal former, in one embodiment, a Formula I compound and a co-crystal former can be ground together followed by melting of the resultant solid mixture and cooling to form co-crystals. Alternatively, the crystal former can be melted prior to contact with a Formula I and the resultant mixture is allowed to co-crystallize. The inventive co-crystals can be obtained by combining a solvate of a Formula I compound with a co-crystal former or by combining a Formula I compound with a solvate of a co-crystal former under conditions suitable to promote co-crystallization.

Assaying the solid mixture for the presence of co-crystals may be carried out by conventional methods known in the art. For example, it is convenient and routine to use powder X-ray diffraction techniques to assay for the presence of co-crystals in a crystallization mixture. Other techniques, used in an analogous fashion, include differential scanning calorimetry (DSC), thermogravimetric analysis (TGA) and Raman spectroscopy. Single crystal X-ray diffraction and solid state NMR methodologies are especially useful in identifying co-crystal structures.

Figure 2:
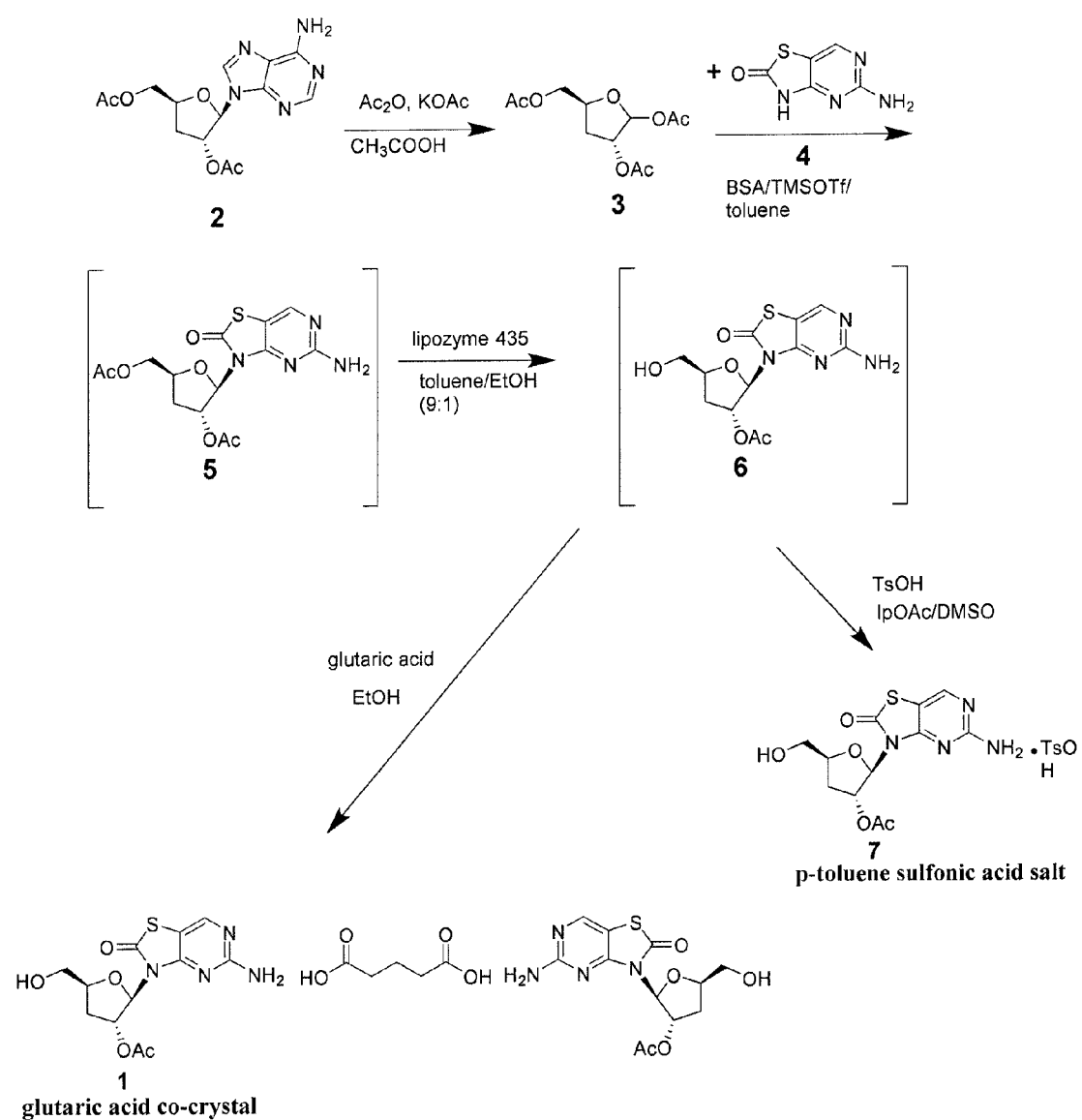
FIG. 2—Exemplary protocol for the synthesis of the Formula I compound and an exemplary co-crystal.

FIG. 2 illustrates the synthesis of a co-crystal comprising a Formula I compound and glutaric acid as an exemplary co-crystal former. For comparative purposes, FIG. 2 also illustrates a method for preparing p-toluene sulfonic acid salt of 5-amino-2-oxothiazolo[4,5-d]pyrimidin-3(2H)-yl-5-hydroxymethyl tetrahydrofuran-3-yl acetate. As illustrated, the synthetic method is operationally simple, robust, efficient, and scalable for commercial production of co-crystals. Furthermore, the method is cost-effective and permits the manufacture of co-crystals in good yield.

Briefly, deoxyadenosine (2) is depurinated under acidic conditions. In one embodiment, depurination is achieved by contacting compound 2 with acetic anhydride, potassium acetate and glacial acetic acid to form (3R,5S)-5-(methylacetoxytetrahydrofuran)-2,3-diyl diacetate (3).

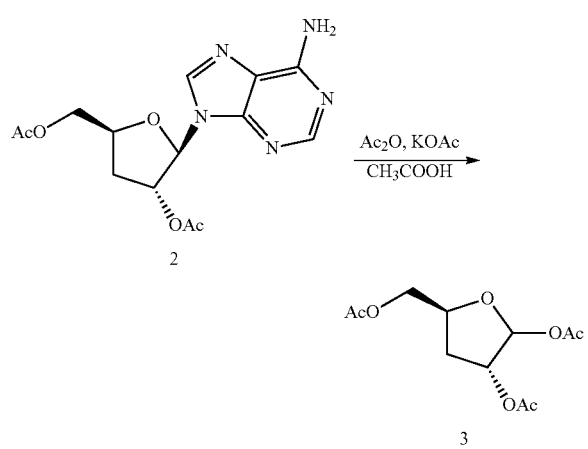

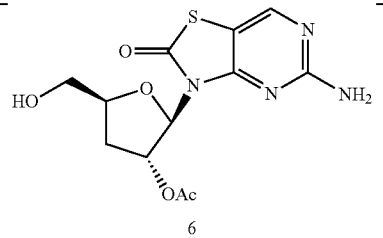

Compound 3 is then coupled to 5-amino-3H-thiazolo[4,5-d]pyrimidin-2-one (4) [prepared according to the method of Wolfe et al. *J. Org. Chem.* 1997, 62, 1754-1759] in the presence of tetramethylsilyl trifluoromethane sulfonate (TMSOTf) to form compound 5. While TMSOTf is exemplified as the acid catalyst for coupling compound 3 to compound 4, other acid catalysts such as $AlCl_3$, $SnCl_4$ and $TiCl_4$ together with a silating reagent such as N,O-bis(trimethylsilyl) acetamide ("BSA") or trimethylsilyl chloride also can be used. Typically, stoichiometric amounts of compounds 3 and 4 are used for the coupling reaction. However, a slight excess of the 5-amino-3H-thiazolo[4,5-d]pyrimidin-2-one (4) can be used for the synthesis of compound 5. According to an aspect, the range for the molar ratio of 5-amino-3H-thiazolo[4,5-d]pyrimidin-2-one (4) to compound 3 is from about 1.2:1 to about 10:1, from about 1.2:1 to about 9:1, from about 1.2:1 to about 8:1, from about 1.2:1 to about 7:1, from about 1.2:1 to about 6:1, from about 1.2:1 to about 5:1, from about 1.2:1 to about 4:1, from about 1.2:1 to about 3:1, or from about 1.2:1 to about 2:1, Selective de-acetylation of the 5-methylacetoxy group is achieved by incubating compound 5 with lipozyme 435.

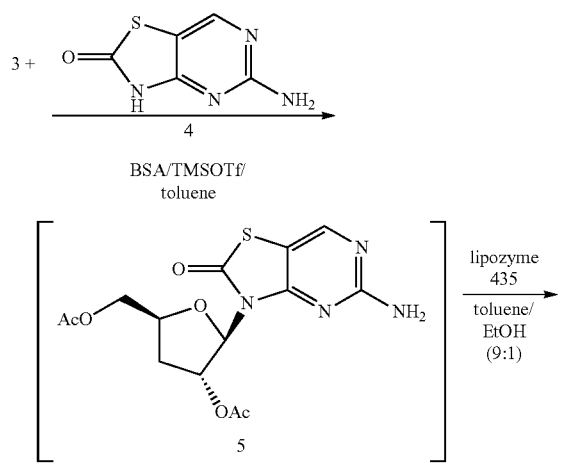

Enzyme catalyzed deacetylation is carried out by adding a buffered solution of the enzyme to an organic solution of compound 5. Alternatively, the enzyme may be covalently attached to a solid support and selective de-acetylation is achieved by contacting the solid-supported enzyme with an organic solution of compound 5. The use of a solid supported enzyme is advantageous because it permits efficient recycling of the enzyme and allows for shorter reaction times.

Compounds such 5-amino-2-oxothiazolo[4,5-d]pyrimidin-3 (2H)-yl-5-hydroxymethyl tetrahydrofuran-3-yl acetate (6) are difficult to handle. Evaporation of the reaction solvent or precipitation of compound 6 from the reaction mixture is difficult and moreover, provides a sub-optimal product that is unsuitable for co-crystal formation. The method according to the present disclosure eliminates the need for isolating compound 6 because the reaction mixture contains compound 6 in a state of purity and in a solvent mixture that is suitable for initiating co-crystals. Co-crystals in accordance with the invention, therefore, can readily be obtained by contacting the reaction mixture containing compound 6 with a co-crystal former (solid), or a solution of a co-crystal former.

According to one embodiment, formation of co-crystals is initiated by ageing a reaction mixture comprising compound 6 and a co-crystal former at an ambient temperature. For example, the reaction mixture may be aged at a temperature from about −10° C. to about 35° C., from about 10° C. to about 25° C., or at a temperature from about 10° C. to about 20° C.

If cooling is necessary to initiate co-crystal formation, the temperature of the co-crystallization mixture may be cooled at a rate of about 1° C. per minute, about 0.5° C. per minute, or about 0.25° C. per minute. For some embodiments, the temperature of the cold reaction mixture is in a range from about −20° C. to about 20° C., for instance from about −20° C. to about −10° C., from about −10° C. to about 0° C., from about 0° C. to about 5° C., or from about 0° C. to about 10° C.

Other techniques for preparing co-crystals in accordance with the invention include without limitation mechanical co-crystal synthesis, solvothermal co-crystal synthesis, the use of solvent evaporation for co-crystal synthesis, solid state grinding method for co-crystal synthesis and solvent drop grinding method for co-crystal synthesis.

The synthesis of co-crystals by the solvent evaporation method includes preparing separate solutions of the Formula I compound and appropriate co-crystal former, mixing stoichiometric amount of a solution of the Formula I compound with a stoichiometric amount of a solution of the co-crystal former and super saturating the resultant reaction mixture comprising the Formula I compound and co-crystal former by storing the reaction mixture at a temperature suitable for initiating co-crystal formation.

According to one embodiment, the inventive co-crystals were obtained by the solvent drop grinding method. Briefly, the Formula I compound (compound 6) and the co-crystal former were ground together in the presence of small quantities of an appropriate co-crystallization solvent which is believed to function as a catalyst.

Solvents suitable for co-crystal formation include, for example, ethanol, methanol, n-propanol, isopropanol, n-butanol, isobutanol, ethyl acetate, acetonitrile, isopropyl acetate, THF and mixtures thereof. In one embodiment, an ethanol solution of glutaric acid was added to a toluene-ethanol solution of compound 6. The resultant super-saturated reaction mixture was then cooled to form 5-amino-2-oxothiazolo[4,5-(1]pyrimidin-3 (2H)-yl-5-hydroxymethyl tetrahydrofuran-3-yl acetate glutaric acid co-crystals.

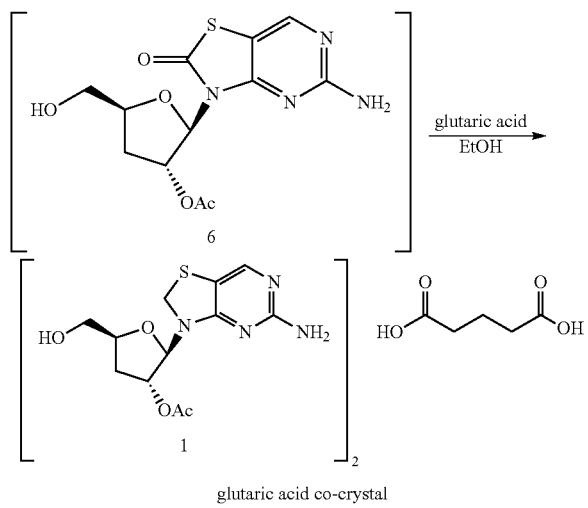

glutaric acid co-crystal

Typically, an equimolar or a greater molar amount of co-crystal former is used to synthesize co-crystals. Depending on the reaction stoichiometry, the molar ratio of co-crystal former to a Formula I compound can be about 1:1, 1:2, or about 2:1. The concentration of the solution of compound 6 and the solution of a co-crystal former can vary from about 50 millimolar to about 2.0 molar, for example about 250 millimolar, about 500 millimolar, about 600 millimolar, about 700 millimolar, about 800 millimolar, about 900 millimolar, about 1 molar, about 1.2 molar, about, 1.4 molar, about 1.6 molar, about 1.8 molar or about 2.0 molar.

The formation of co-crystals depends on the concentration of the solution of the co-crystal former, the concentration of the solution of the Formula I compound, the solubility of the reactants (co-crystal former and Formula I compound) and product (co-crystal) in the reaction mixture at a temperature suitable for initiating co-crystal formation. Typical co-crystallization times can vary from about 10 minutes to about 48 hours, from about 10 minutes to about 24 hours, from about 10 minutes to about 12 hours, from about 10 minutes to about 10 hours, from about 10 minutes to about 8 hours, from about 10 minutes to about 6 hours, from about 10 minutes to about 4 hours, from about 10 minutes to about 2 hours, or from about 10 minutes to about 1 hour.

Co-crystals thus formed can be isolated by gravity filtration, vacuum filtration followed by washing of the isolated co-crystals and drying. Co-crystals may also be isolated by evaporating the solvent from the reaction mixture. Isolated co-crystals are typically dried at a temperature from about 30° C. to about 70° C. or from about 40° C. to about 60° C. The drying method may be carried out at atmospheric pressure or under reduced pressure (vacuum), for example, a reduced pressure range from about 0.1 to about 10 millimeters of mercury.

The method disclosed above has provided co-crystals in accordance with the present invention having a purity of at least 95%, 96%, 97%, 98%, 99%, 99.5%, 99.6%, 99.7%, 99.8%, or 99.9%. The following exemplary co-crystals were synthesized using a method of the invention.

EXAMPLES

The following synthetic protocols examples are for illustrative purposes only and are not intended to limit the scope of the claims.

In the synthetic schemes described below, unless otherwise indicated all temperatures are set forth in degrees Celsius and all parts and percentages are by weight. Reagents were purchased from commercial suppliers and were used without further purification unless otherwise indicated. All solvents were purchased from commercial suppliers and were used as received.

The reactions set forth below were done generally under a positive pressure of nitrogen or argon at an ambient temperature (unless otherwise stated) in anhydrous solvents, and the reaction flasks were fitted with rubber septa for the introduction of substrates and reagents via syringe. Glassware was oven dried and/or heat dried. The reactions were assayed by TLC and/or analyzed by LC-MS and terminated as judged by the consumption of starting material. Analysis by Ultra performance liquid chromatography (UPLC) was performed using a High Strength Silica (HSS) column or an YMC column (Waters®). Typical flow rates are between 0.7 mL to 1.0 mL/minute and the injection volumes are about 2-5 μL.

Analytical thin layer chromatography (TLC) may be performed on glass-plates precoated with silica gel 60 F$_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution.

$^1$H-NMR spectra and $^{13}$C-NMR were recorded on a Bruker Avance II® spectrometer operating at 600 MHz. NMR spectra were obtained as CDCl$_3$ solutions (reported in ppm), using chloroform as the reference standard (7.27 ppm for the proton and 77.00 ppm for carbon), CD$_3$OD solutions using 3.4 ppm and 4.8 ppm as reference standards for the protons and 49.3 ppm as a reference standard for carbon, DMSO-d$_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Synthesis of a glutaric acid co-crystal of 5-amino-3-(2'-O-acetyl-3'-deoxy-β-D-ribofuranosyl)-3H-thiazolo[4,5]pyrimidine-2-one)

A. Coupling Reaction—Synthesis of (2S,4R,5R)-4-acetoxy-5-(5-amino-2-oxothiazolo[4,5-d]pyrimidin-3(2H)-yl-tetrahydrofuran-2-yl-methyl acetate (5)

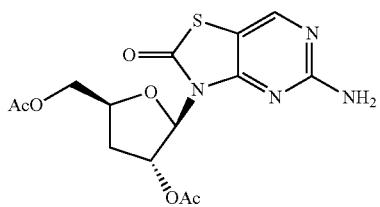

Compound 5 was synthesized following the protocol described in PCT publication No: WO2008140549. Briefly, a three necked flask equipped with a temperature probe, condenser and nitrogen inlet is charged with 5-amino-3H-thiazolo[4,5-d]pyrimidine-2-one (compound 4) and acetonitrile. N,O-bis(trimethylsilyl) acetamide (BSA) was added via a funnel to the solution of compound 4 followed by stirring at 40° C. for 90 minutes under an atmosphere of nitrogen. After cooling to 5° C. a solution of 1,2,5-tri-O-acetyl-β-D-ribofuranose (compound 3) in acetonitrile is added, followed by the addition of TMSOTf.

The reaction mixture was then heated to 75° C. and maintained at this temperature for ten hours. After heating the flask containing the reaction mixture was gradually cooled to 15° C. Water was then added to the cold reaction mixture in one mL portions to quench the reaction while maintaining the temperature of the reaction mixture at 15° C. The quenched reaction mixture is combined with celite and neutralized using sodium hydroxide. The filtrate obtained upon removal of celite was combined with an aqueous solution of sodium bicarbonate and solid sodium chloride prior to its transfer to a separatory funnel and extraction with acetonitrile. Concentration of the organic layers gave the desired product, compound 5. The identity of compound 5 and its purity were determined by HPLC using authentic material as the standard.

B. Selective De-Acetyaltion—Synthesis of Compound 6

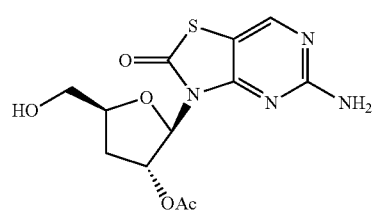

A solution of compound 5 in acetonitrile is added to an aqueous bicarbonate solution of *Candida antarctica*, type B (Biocatalytics catalog number IMB-111) lipase bound to a solid support. The reaction mixture (suspension) was stirred for 36 hours, followed by filtration of the enzyme linked support. The filtrate was extracted with ethyl acetate. The combined ethyl acetate layers were dried using anhydrous magnesium sulfate, stirred with Norit 211 for 90 minutes and then filtered through a celite filter aid to obtain the desired alcohol (6). The identity of compound 6 and its purity were determined by HPLC using authentic material as the standard.

C. Co-Crystal Formation

An ethyl acetate solution (47.4 mL) containing 17.2 g of compound (6) [52.7 mmoles], was subjected to rotary evaporation at 60° C. under a reduced pressure of 180 mbars to remove solvent. The residue thus obtained was dissolved in ethanol (110 mL) and concentrated under reduced pressure (60° C., 180 mbars). Fresh ethanol (83 mL) was then added to the reaction mixture in a round bottom flask and the mixture was stirred at room temperature until a clear yellow ethanol solution of compound (6) is obtained.

A solution of glutaric acid (3.62 g, 27.4 mmoles) was prepared by dissolving glutaric acid in 15 mL of ethanol. The clear colorless solution was then added drop-wise over a period of 15 minutes to a stirring ethanol solution compound (6) that was heated and maintained at a temperature 50° C. during the addition of glutaric acid. The co-crystallization mixture was then cooled to 30° C. at a rate of 0.25° C./min to initiate co-crystal formation. No crystals were formed after stirring of the cold co-crystallization mixture.

The co-crystallization mixture was re-heated to 50° C. with stirring. 10 mg of a glutaric acid co-crystal of a Formula I compound was added to the co-crystallization mixture as seed to initiate co-crystal formation and the mixture cooled at a rate of 0.25° C./min. As the temperature dropped a thick suspension that could not be stirred was formed. The co-crystallization mixture was re-heated to 55° C. and maintained at this temperature until a suspension that can easily be stirred was obtained.

The hot, stirring suspension was then cooled gradually to about 0° C. by lowering the temperature at a rate of 0.25° C./min. The cold co-crystallization mixture was stirred overnight while maintaining the temperature of the co-crystallization mixture between 0° C. and 5° C. The suspension of co-crystals were collected by suction filtration, washed with cold ethanol (43 mL), and dried in a vacuum oven (<5 mbar) at a temperature of 40° C. Yield—18.24 g (88.1%) of glutaric acid co-crystals was obtained as a white solid. The purity of the co-crystals was determined by HPLC and was found to be 99.75% pure.

Table 10 illustrates exemplary co-crystals that were synthesized using a protocol similar to the one disclosed in Example 1 and the corresponding physical characteristics of the exemplified co-crystals.

TABLE 10

| Co-Crystal Former | BCS Class (Stahl et al) | Salt factor |
|---|---|---|
| Fumaric acid | 1 | 1.18 |
| Malonic acid | 2 | 1.16 |
| Glutaric acid | 1 | 1.2 |
| Adipic acid | 1 | 1.22 |
| Glycolic acid | 1 | 1.12 |
| 2-aminobenzoic acid | — | 1.42 |
| α-ketoglutaric acid | 1 | 1.45 |

As illustrated above, the salt factor (S) of the inventive co-crystals are lower than the salt factor for the tosylate salt of the Formula I compound ($S_{Tos}$ is 1.53). Because of their lower S-value compositions comprising the co-crystals achieve higher steady state plasma concentrations of the Formula I compound at lower oral doses. Consequently, a patient undergoing therapy will require fewer oral doses of a composition of the co-crystal to achieve therapeutically appropriate plasma concentrations of the Formula I compound than a patient receiving a composition of the tosylate salt of the Formula I compound.

V. Inhibition of HBV Viral Replicon Replication Activity

HBV infection is one of the leading causes of acute and chronic liver disease. While current HBV treatments are effective at reducing serum HBV DNA levels, these therapeutic agents have limited effectiveness at lowering viral clearance rates and often require prolonged use which causes severe toxic side effects. The present invention provides co-crystals of a Formula I compound as agonists of Toll like receptor 7 (TLR-7), which is expressed on immature dendritic cells.

TLR's are a family of pathogen-recognition receptors that activate immune responses by stimulating the release of cytokines and chemokines in a host. The cytokines and chemokines released upon the activation of a hosts' immune system are effective anti-viral agents, primarily due to their ability to recognize and kill viral infected cells. Accordingly, co-crystals of a Formula I compound (double prodrug), the single prodrugs (de-acetylated Formula I compound or the oxidized form of a Formula I compound) and the un-acetylated, oxidized form of a Formula I compound (bioactive species) were each evaluated for their ability to inhibit HBV replication in vitro. Scheme 1 (above), illustrates the structure of the double prodrug, the structure of the single prodrugs and the bioactive species.

Direct inhibition of viral replication was evaluated by monitoring the levels of secreted HBV DNA and the levels of HBV surface antigen (HBsAg) in cultures containing HBV infected HepaRG cells. Inhibition of viral replication in culture also was evaluated indirectly by exposing HBV infected HepaRG cells to conditioned medium from peripheral blood mononuclear cells (PBMC's) stimulated by the un-acetylated, oxidized form of a Formula I compound (bioactive species), which is a selective TLR-7 agonist.

Generation of HepaRG Cell Line

HepaRG cells (Cat# HPR101), HepaRG Growth Medium Supplements (Cat# ADD710), and HepaRG Differentiation Medium Supplements (Cat# ADD720) were purchased from Biopredics International (Rennes, France). While there is no DMSO in the Growth Medium Supplements, the Differentiation Medium Supplements contains 2% DMSO. Cells were cultured at 37° C. in a humidified atmosphere with 5% $CO_2$ in William's E Medium (WEM) (GIBCO) containing Growth Medium Supplements. To initiate differentiation, growth medium was combined with differentiation medium (WEM containing Differentiation Medium Supplements) in a 1:1 ratio and added to confluent HepaRG cells.

After three days incubation, the combined medium was replaced with differentiation medium and the cells were maintained in the differentiation medium for an additional 2 to 4 weeks. The differentiation medium was renewed every 2 to 3 days throughout the incubation period. Differentiated HepaRG cells (HepaRG$_d$) display hepatocyte-like cell islands surrounded by monolayer of biliary-like cells. Prior to HBV infection and compound treatment, HepaRG$_d$ cells were seeded into collagen I coated 96-well plates (Gibco, Cat# A11428-03) at 50,000 to 60,000 cells per well. Cells were allowed to recover their differentiated phenotype in 96-well plates for at least 1 week after plating prior to HBV infection.

HBV Infection

HBV inoculum was collected from HepG2.2.15 cultured cells, a cell line that supports HBV (genotype D, strain ayw) replication and virion secretion as disclosed in Sells M A., et al., PNAS, 84(4): 1005-1009. HepG2.2.15 cells were maintained in DMEM+GlutaMAX-I (Invitrogen) containing 1× Pen/Strep (Invitrogen), 10% FBS, and 0.25 mg/ml G-418 (Invitrogen) using hyperflasks (Corning) pre-coated with collagen I (BD Biosciences). Upon reaching confluency, HepG2.2.15 culture media was replaced with DMEM+GlutaMAX-I containing 1× Pen-Strep, 2.5% FBS, and 1% DMSO for 3 days and then replaced with DMEM+GlutaMAX-I containing 1× Pen-Strep and 1% DMSO. The 1% DMSO containing media was collected every 3 to 4 days over a two week period and HBV infectious virions and subviral particles were pelleted by ultracentrifugation through a 20% sucrose cushion in a Ti 45 Beckman rotor at 45,000 rpm for 3 hours at 4° C. The pellets were resuspended in WEM at a concentration of $10^8$-$10^9$ genome equivalents (GE) per ml, determined by real time PCR as described below using a genotype D HBV containing plasmid DNA as an internal standard. To evaluate the infectivity of the inoculum, HepaRG$_d$ cells in 96-well plates were infected in differentiation medium containing 50 to 200 GE/cell and 4% PEG 8000 (PolyEthylene Glycol 8000, Sigma, Cat# P5413-500G) for 16 hr at 37° C. At the end of the infection, HBV inoculum was removed and cells were washed 3 times with differentiation medium. Differentiation medium was replenished every 2 to 3 days and HBV replication was monitored by measuring secreted HBV DNA, hepatitis B surface (HBsAg) and/or e (HBeAg) antigens.

Detection of Secreted HBV Antigens and HBV DNA

HBsAg was detected from 50 μL of HBV infected HepaRG supernatants using the HBsAg chemiluminescence immunoassay (CLIA) kit following instructions as recommended by the manufacturer (Autobio Diagnostics Co., Zhengzhou, China). HBV DNA was extracted from 50 μL of HBV infected HepaRG$_d$ supernatants using the MagNA Pure 96 DNA and Viral NA Small Volume Kit (Roche, Cat#05 467 497 001). A 99 nucleotide fragment covering the core region was amplified with forward primer CTG TGC CTT GGG TGG CTT T, reverse primer AAG GAA AGA AGT CAG AAG GCA AAA, and probe 56-FAM-AGC TCC AAA/ZEN/TTC TTT ATA AGG GTC GAT GTC CAT G-3IABkFQ (IDT DNA) using the EagleTaq Master Mix Kit (Roche, Cat#05529026 190) and the following heating/cooling cycles condition: 2 min at 50° C., 10 min at 95° C., and 40 cycles of 95° C. for 15 sec and 60° C. for 1 min. All PCR reactions were performed using the ViiA7 Real Time PCR system (Life Technologies).

Inhibition of HBV Viral Replication

Co-crystals of a Formula I compound in accordance with the invention are double prodrugs that are enzymatically converted in vivo to the biologically active species 5-amino-3-((2R,3R,5S)-3-hydroxy-5-(hydroxymethyl)tetrahydrofuran-2-yl)-3a,7a-dihydrothiazolo[4,5-d]pyrimidine-2,7(3H,6H)-dione as illustrated in Scheme 1 above. These compounds are believed to exert anti-viral activity by stimulating the toll like receptors, particularly TLR-7 to release cytokines and chemokines. To determine the viral replication inhibitory activity, the glutaric acid co-crystal (double prodrug), the de-acetylated form of the Formula I compound (single prodrug) and the biologically active species (R06871765) were synthesized.

Both direct and indirect inhibitory activity of HBV replication was measured. Roferon-A, IL-6, TNF-α, IP-10 or DMSO were used as no drug controls in the study. For the direct study stock solutions of the glutaric acid co-crystal, the de-acetylated form of the Formula I compound, and the biologically active species (R06871765) as well as the control agents were prepared in WEM growth medium at a final volume of 120 μL and DMSO concentration of 2% (v/v). Aliquots of these reagents were added to independent wells of a 96-well culture plate containing HBV infected HepaRG$_d$ cells on day 4 post infection. The final concentration of DMSO in each well was 2%. The HepaRG$_d$ cells used in the inhibition study were maintained in differentiation media containing 2% DMSO. To evaluate the indirect inhibitory activity of HBV replication, HBV infected HepaRG$_d$ cells were incubated with conditioned media collected from DMSO (control) or R06871765 (100 μM) stimulated PBMCs, serially diluted in differentiation media.

HBV viral replication inhibitory activity were carried out by adding a known aliquot of differentiation media containing a test compound or an aliquot of the conditioned media to HBV infected cells in culture. Known aliquots of differentiation media containing a test compound or conditioned media were added every 2 to 3 days to HBV infected cells in culture for a total of 7 days. On day 7 of treatment (11 days post infection), 50 μL of the supernatant was used to determine levels of secreted HBV antigens or HBV DNA using CLIA or real time PCR, respectively, as described above. Cell viability was determined using CellTiter-Glo (Promega, Cat# G7571). Dose-response curves were obtained by using Graphpad (La Jolla, Calif.). The $EC_{50}$ (Effective concentration causing 50% inhibition) and $CC_{50}$ (untreated cell control) values were calculated from the dose-response curves as the concentration of a test compound or the concentration of conditioned media (log dilution) at which a 50% reduction in HBV viral replication activity is observed compared to no drug controls. The $EC_{50}$ and $CC_{50}$ values were derived from 2-4 independent HBV infection studies, each performed in duplicate.

Direct Effect of R06871765 on HBV Replication

Previous viral inhibition studies had shown that the glutaric acid co-crystal (double prodrug), and the de-acetylated form of the Formula I compound (single prodrug) did not inhibit viral replication in cultured HepaRG cells. To evaluate whether R06871765 (biologically active species) inhibits HBV viral replication in HepaRG cells, infected cells were incubated with known concentrations of R06871765 on day 4 post infection. Serial dilution of a 200 μM stock solution of R06871765 was used for preparing test solutions. The concentrations of R06871765 tested in the viral inhibitory study were—200 μM, 66.67 μM, 22.22 μM, 7.41 μM, 2.47 μM and 0.82 μM. Cell medium was replenished with fresh medium containing a known concentration of R06871765 or 2% DMSO (control cells) every 3 days. HBV infected HepaRG$_d$ cells treated with pegylated interferon-alpha 2a (Pegasys®) at three different concentrations of 56 pM, 167 pM, and 500 pM was used as the positive control.

Figure 3A:
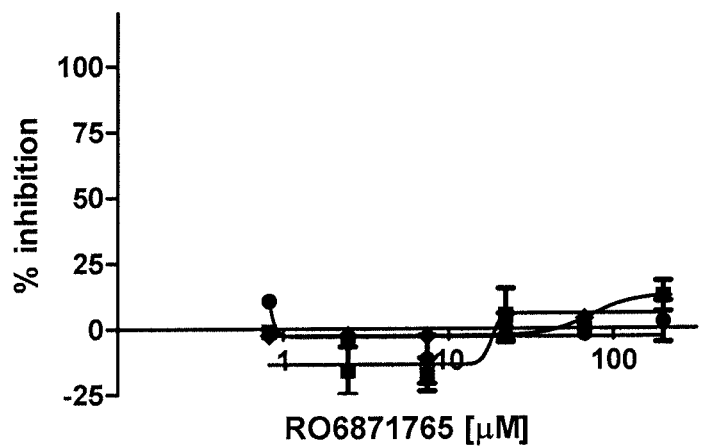
FIG. 3A—Effect of biologically active species (RO6871765) on HBV replication. HBV replication was monitored by measuring levels of secreted HBV DNA (■) and HBsAg (●) using real time PCR and CLIA assays, respectively. Cell viability was determined by CellTiter-Glo (▲).

Levels of secreted HBsAg and HBV DNA were measured on day 7 of the treatment (11 days post infection of cells). As shown in FIG. 3A, R06871765 did not exert any direct anti-HBV effect. No changes in levels of HBV DNA or HBsAg, were detected for cells incubated with the highest concentration (200 μM) of R06871765. Accordingly, the $EC_{50}$ of R06871765 is greater than 200 μM (FIG. 3A, Table 11). No significant cytotoxicity was observed when HBV infected HepaRG$_d$ cells were treated with R06871765 ($CC_{50}$>200 μM, maximum reduction in viability is about 17% at highest concentration of R06871765).

TABLE 11

| Conc. (μM) | HBsAg (% inhibition) | | | HBV DNA (% inhibition) | | Cell viability (% inhibition) | |
|---|---|---|---|---|---|---|---|
| 200 | 2.48 | 4.25 | 15.99 | 12.16 | 3.11 | 12.31 | 21.99 |
| 66.67 | -2.13 | 14.49 | 5.02 | -0.65 | 21.06 | 3.70 | 7.34 |
| 22.22 | 0.44 | 3.98 | 0.66 | 4.96 | 5.69 | -2.43 | -1.37 |
| 7.41 | -11.72 | 3.92 | 1.81 | -17.43 | -23.53 | -2.85 | -1.50 |
| 2.47 | -4.70 | 11.83 | 14.69 | -15.96 | -0.77 | -2.57 | 0.54 |
| 0.82 | 10.48 | 14.67 | 14.80 | -1.24 | 12.23 | -2.58 | 3.23 |
| EXP ID | 10/15/2012 AL | 10/15/2012 VL | 11/1/2012 | 10/15/2012 AL | 11/1/2012 | 10/15/2012 AL | 10/15/2012 VL |
| $EC/CC_{50}$ (μM) | >200 | >200 | >200 | >200 | >200 | >200 | >200 |

Figure 3B:
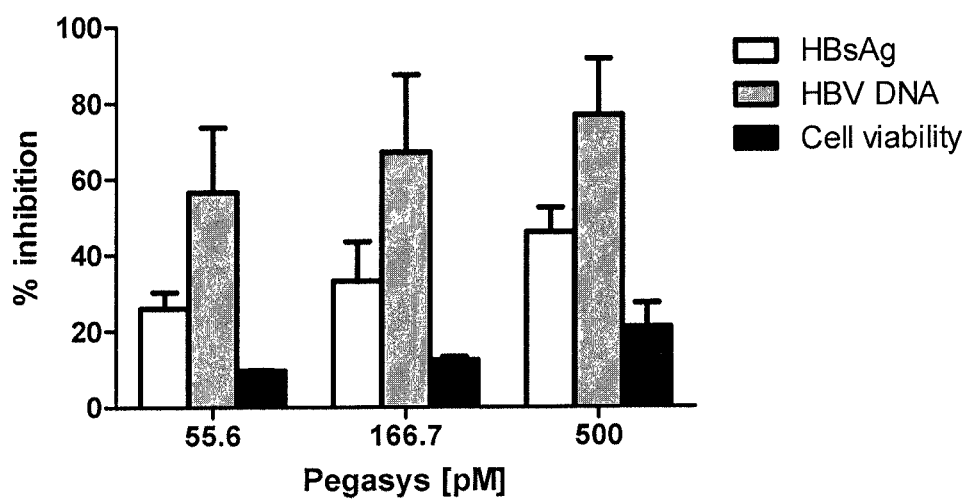
FIG. 3B—Effect of pegylated interferon-α-2a (Pegasys®) on HBV replication. HBV replication was monitored by measuring levels of secreted HBsAg (white bars) and HBV DNA (grey bars) using CLIA and real time PCR assays, respectively. Cell viability was determined by CellTiter-Glo (black bars).

In contrast, HBV infected HepaRG$_d$ cells treated with pegylated interferon-alpha 2a showed a significant reduction of HBV replication. The levels of secreted HBV DNA and HBsAg were reduced by 76.9%±14.8% and 46.0%±6.3%, respectively, at the highest concentration tested (500 pM; see FIG. 3B, Table 12).

TABLE 12

| Pegasys | % inhibition ± SD | | |
|---|---|---|---|
| [pM] | HBV DNA (n = 4) | HBsAg (n = 4) | Cell viability (n = 3) |
| 500 | 76.9 ± 14.8 | 46.0 ± 6.3 | 21.0 ± 6.3 |
| 166.7 | 67.1 ± 20.3 | 33.1 ± 10.3 | 12.4 ± 1.0 |
| 55.6 | 56.5 ± 17.2 | 25.9 ± 4.2 | 9.6 ± 0.1 |

These results indicate that R06871765 has poor anti-viral activity. To the surprise of the inventors, however, conditioned medium obtained from R06871765 stimulated PBMC's significantly reduced both HBV DNA and HBsAg secretions from HBV infected cultured HepaRG cells, thus, providing support for an indirect inhibition of HBV viral replication by R06871765.

Indirect Effect of R06871765 on HBV Replication

TLR-7 agonists stimulate the production cytokines and chemokines from human PBMC's. Conditioned medium was obtained by contacting cultured PBMC's with DMSO (control) or 100 μM R06871765 (drug) was contacted with HBV infected HepaRG$_d$ cells.

HBV infected HepaRG$_d$ cells were incubated with various dilutions of conditioned media collected from PBMCs isolated from healthy donors—donor 70615 (graphs A-D) and donor 77726 (graphs E, F). The PBMC's from each donor were stimulated with either DMSO (graphs A, C, E) or 100 μM R06871765 (graphs B, D, F). FIGS. 4A, 4C and 4E correspond to inhibition of HBV viral replication using DMSO stimulated PBMC's while FIGS. 4B, 4D and 4F correspond to inhibition of HBV viral replication using R06871765 stimulated PBMC's. Three experiments were performed. In the first experiment (FIGS. 4A, 4B), conditioned media from PBMCs (donor 70615) was first diluted 10-fold using differentiation media, and then serially diluted in 3-fold increments prior to addition of each of the diluted conditioned medium to HBV infected HepaRG$_d$ cells. In the second experiment (FIGS. 4C, 4D), conditioned media from PBMCs (donor 70615) was first diluted 5-fold using differentiation media, and then serially diluted in 5-fold increments prior to addition to HBV infected HepaRG$_d$ cells. In the third experiment (FIGS. 4E, 4F), conditioned media from PBMCs (donor 77726) was first diluted 5-fold using differentiation media, and then serially diluted in 5-fold increments prior to addition to HBV infected HepaRG$_d$ cells. The HBV replication inhibitory activity for control and R06871765 treated cells was determined by monitoring the levels of HBV DNA and HBsAg secreted in culture medium.

Figure 4:
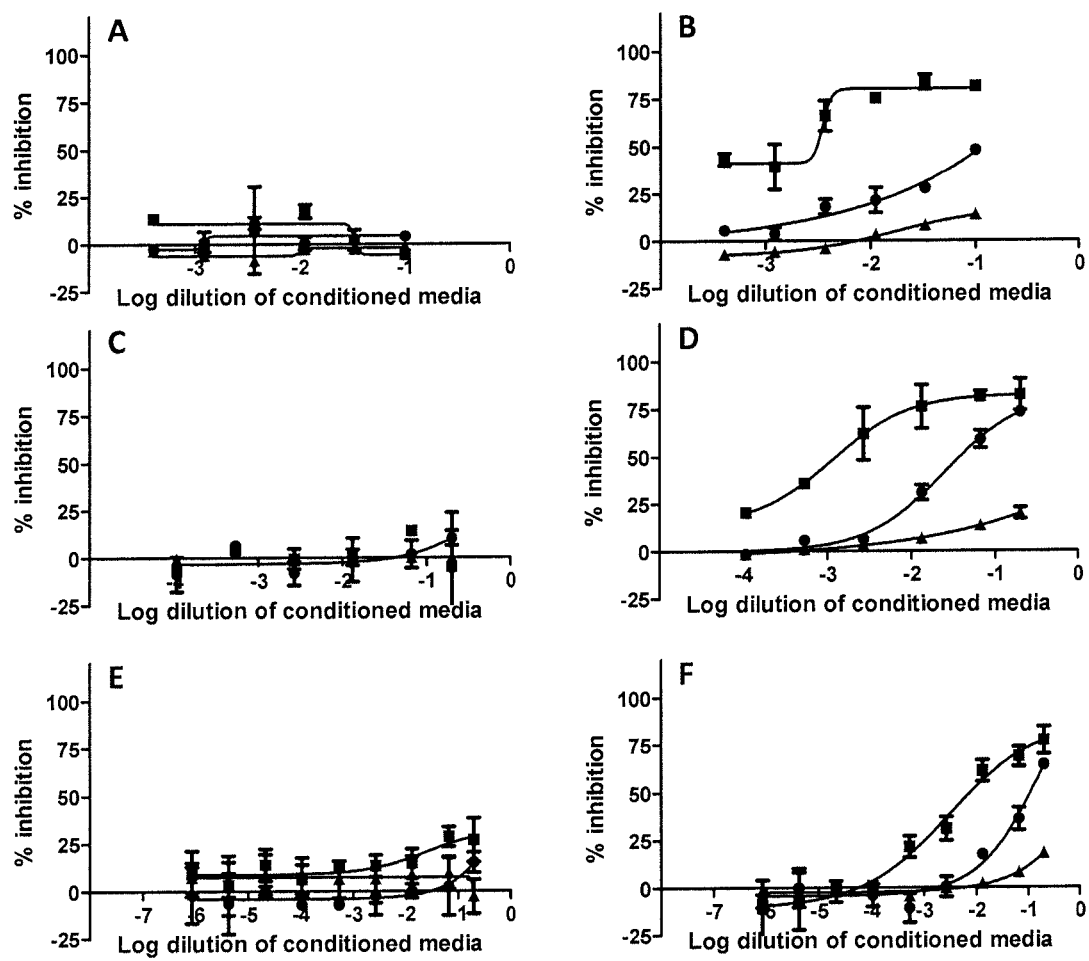
FIG. 4—Effect of DMSO or RO6871765 stimulated PBMC conditioned medium on HBV replication. DMSO conditioned medium—Graphs (A), (C) and (E). RO6871765 (100 μM) stimulated PBMC conditioned medium—Graphs (B), (D) and (F). HBV replication was monitored by measuring levels of secreted HBV DNA (■) and HBsAg (●) using real time PCR and CLIA assays, respectively. Cell viability was determined by CellTiter-Glo (▲).

As illustrated in FIG. 4, conditioned media from PBMCs treated with DMSO did not induce any significant antiviral effect (See FIGS. 4A, 4C and 4E and Table 13). In contrast, a dose-dependent reduction of both secreted HBV DNA and HBsAg levels was observed in the presence of conditioned media from PBMC's treated with R06871765 (See FIGS. 4B, 4D and 4F, Table 13). The average EC50 value of R06871765 against HBV DNA was −2.5±0.4 log$_{10}$, which is equivalent to a 1:318 dilution of the R06871765 stimulated conditioned media (Table 13). The average EC50 value for the R06871765 stimulated conditioned media against the HBV surface antigen (HBsAg) secretion was −1.2 log$_{10}$, which is equivalent to a 1:16 dilution (Table 13). Cell viability assay showed that conditioned media from DMSO treated-PBMCs displayed no significant cytotoxic effect, while HBV infected HepaRGd cells treated with diluted conditioned media (10-fold and 5-fold dilutions) from R06871765 stimulated PBMCs showed a slight reduction in cell viability of 14% and 19%, respectively (FIG. 4, Table 13).

ng/ml for IL-6, TNF-α and IP-10, which were subsequently converted to molar concentrations for comparison.

Figure 5:
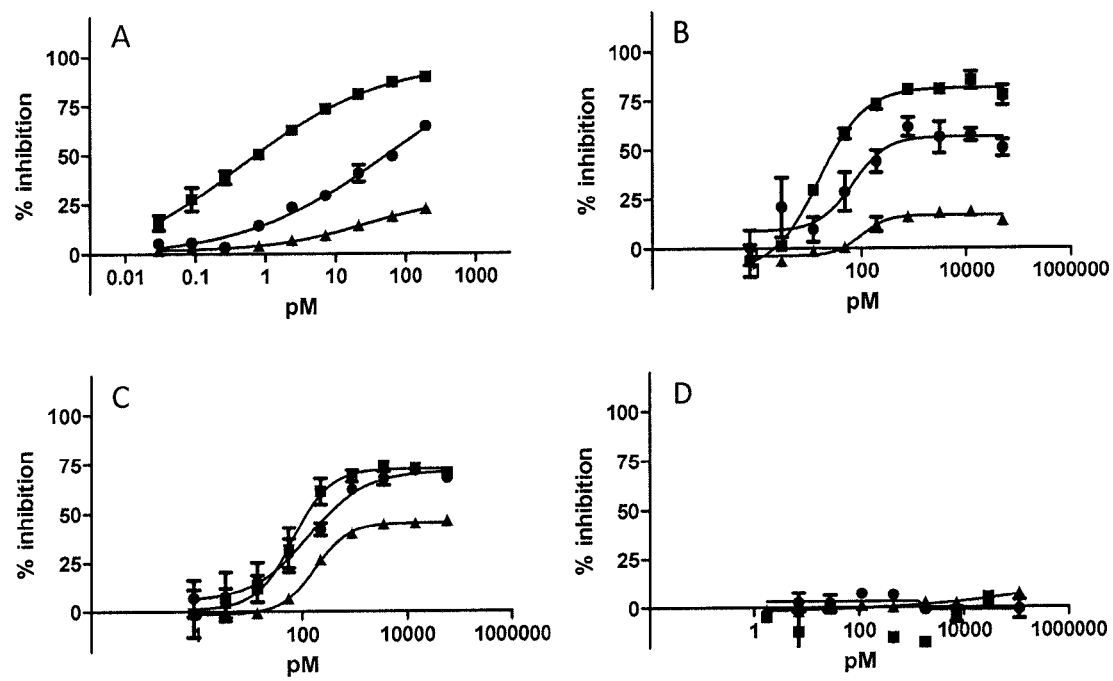
FIG. 5—Effect of IFN-α 2a (Roferon-A), FIG. 5A; IL-6, FIG. 5B; TNF-α, FIG. 5C; and IP-10, FIG. 5D; on HBV replication. HBV replication was monitored by measuring levels of secreted HBV DNA (■) and HBsAg (●) using real time PCR and CLIA assays, respectively. Cell viability was determined by CellTiter-Glo (▲).

As illustrated in FIG. 5, both Roferon-A and IL-6 showed a dose-dependent inhibition of secreted HBsAg and HBV DNA. The EC$_{50}$ values against HBV DNA secretion for Roferon-A and IL-6 are 1.0±0.3 pM and 0.027±0.0073 nM respectively. Roferon-A and IL-6 also inhibit secretion of HBsAg with EC$_{50}$ values of 0.033±0.022 nM and 0.26±0.020 nM respectively. While TNF-α appears to inhibit HBV replication, this cytokine is cytotoxic even at a concentration of about 1 nM. The EC$_{50}$ values for TNF-α against HBV DNA and HBsAg secretion were 0.085±0.046 nM and 0.32, respectively. No cellular toxicity or HBV replication inhibitory effect was observed for the chemokine IP-10, even at the highest concentration tested (EC/CC$_{50}$>115 nM, See FIG. 5). Together these data strongly suggest that R06871765-stimulated PBMC conditioned medium inhibited HBV replication through an indirect mechanism of mediating the release of IFNs and cytokines from human PBMCs.

We claim:

1. A co-crystal comprising at least two components:
   (A) A compound according to Formula I or a pharmaceutically acceptable stereoisomer, or tautomer thereof;

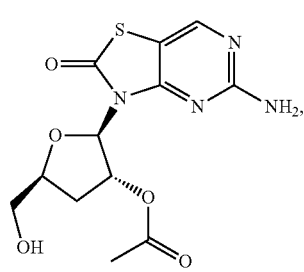

I

TABLE 13

| | conditioned media stimulation | EC$_{50}$ [log dilution] | | | | converted fold dilution |
| --- | --- | --- | --- | --- | --- | --- |
| | | Nov. 12, 2012 donor 70615 | Jan. 3, 2013 donor 70615 | Feb. 28, 2013 donor 77726 | Ave ± SD$^a$ | |
| HBV DNA secretion | DMSO | <−1.0 | <−0.7 | <0.7 | <−0.7 | <5-fold |
| | RO6871765 | −2.5 | −2.9 | −2.1 | −2.5 ± 0.4 | 318 |
| HBsAg secretion | DMSO | <−1.0 | <−0.7 | <−0.7 | <−0.7 | <5-fold |
| | RO6871765 | <−1.0 | −1.4 | −1.0 | −1.2 | 16 |
| | DMSO | <−1.0 | <−0.7 | <−0.7 | <−0.7 | <5-fold |
| | RO6871765 | <−1.0 | <−0.7 | <−0.7 | <−0.7 | <5-fold |

$^a$SD—standard deviation

The anti-viral effect of conditioned medium obtained cultured PBMC's treated with R06871765 most likely is due to the release of cytokines and chemokines from PBMC's. Cytokine profiling studies from conditioned media showed that R06871765 induced release of interferon-α (IFN-α), interleukin 6 (IL-6), tumor necrosis factor alpha (TNF-α), and IFNγ-induced protein 10 (IP-10), while no release of these cytokines was observed when PBMC were treated with DMSO.

To investigate the effect of IFN-alpha 2a (Roferon-A), IL-6, TNF-α, and IP-10 on HBV replication, dose dependent titrations of each of these cytokines were performed using HBV infected HepaRG cell assay. The highest concentrations tested were—1000 IU/ml for Roferon-A and 1000 and
(B) a co-crystal former selected from the group consisting of fumaric acid, malonic acid glutaric acid, adipic acid, glycolic acid, 2-aminobenzoic acid and α-ketoglutaric acid.

2. The co-crystal according to claim 1, wherein the co-crystal comprises the compound of Formula I and glycolic acid.

3. The co-crystal according to claim 1, wherein the co-crystal comprises the compound of Formula I and malonic acid.

4. The co-crystal according to claim 1, wherein the co-crystal comprises the compound of Formula I and fumaric acid.

5. The co-crystal according to claim 1, wherein the co-crystal comprises the compound of Formula I and glutaric acid.

6. The co-crystal according to claim 1, wherein the co-crystal comprises the compound of Formula I and adipic acid.

7. The co-crystal according to claim 1, wherein the co-crystal comprises the compound of Formula I and 2-aminobenzoic acid.

8. The co-crystal according to claim 1, wherein the co-crystal comprises the compound of Formula I and α-ketoglutaric acid.

9. The co-crystal according to claim 1, wherein the compound of Formula I and co-crystal former are present in the co-crystal in a ratio of 1:1, 1:2, or 2:1.

10. The co-crystal according to claim 5, wherein the glutaric acid co-crystal has X-ray powder diffraction peaks at a diffraction angle of 2θ of 5.9, 8.1, 11.3, 11.9, 12.4, 15.7, 17.8, 18.3, 18.9, 20.6, 20.8, 21.6, 22.4, 24.2, 24.6, 25.4, 25.6, 26.5, and 28.6.

11. An anhydrous pharmaceutical composition comprising a pharmaceutically acceptable carrier and a co-crystal comprising at least two components:
(A) A compound according to Formula I or a pharmaceutically acceptable stereoisomer, or tautomer thereof;

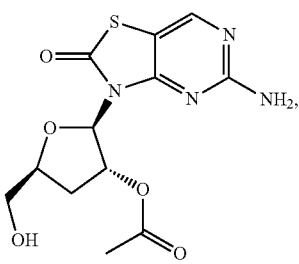

I and
(B) a co-crystal former selected from the group consisting of fumaric acid, malonic acid glutaric acid, adipic acid, glycolic acid, 2-aminobenzoic acid and α-ketoglutaric acid.

12. The pharmaceutical composition according to claim 11, wherein the co-crystal former is glutaric acid.

13. A method for treating a disease or condition comprising administering to a subject in need thereof a therapeutically effective amount of the co-crystal according to claim 1,

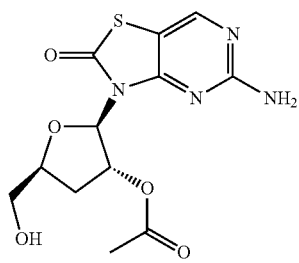

wherein the disease or condition is selected from mammary, colon, bladder, liver, lung, prostate, stomach and pancreas carcinomas or Hepatitis B infection.

14. The method according to claim 13, wherein the disease or condition is Hepatitis B infection.

15. The method according to claim 13, wherein the co-crystal is administered in combination with a therapeutically effective amount of a second therapeutic agent selected from the group of consisting of antibiotics, antiemetic agents, anti-inflammatory agents, antiviral agents, anticancer agents, immunomodulatory agents, α-interferon, β-interferon, pegylated α-interferon, pegylated β-interferon, ribavirin, alkylating agents, hormones, cytokines, polymerase inhibitors, and toll receptor-like modulators.

16. The method according to claim 15, wherein the co-crystal is administered in combination with a therapeutically effective amount of α-interferon, β-interferon, pegylated α-interferon, or pegylated β-interferon.

17. A method for synthesizing a co-crystal comprising:
(i) combining a solution of a co-crystal former with a solution of a compound according to Formula I

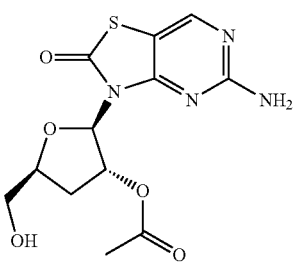

I or a pharmaceutically acceptable steroisomer or tautomer thereof to obtain a co-crystallization mixture; or
(ii) combining a suspension of a co-crystal former with a suspension of a compound according to Formula I

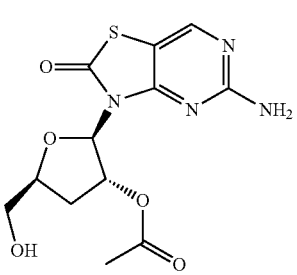

I or a pharmaceutically acceptable steroisomer or tautomer thereof to obtain a co-crystallization mixture; and
(iii) supersaturating the co-crystallization mixture to initiate formation of co-crystals.

18. The method according to claim 17, wherein the solution of the co-crystal former and the solution of the compound of Formula I are obtained using an organic solvent, water, or a mixture of water and an organic solvent.

19. The method according to claim 18, wherein the organic solvent is selected from methanol, ethanol, propanol, isopropanol, isopropyl acetate, hexane, heptane, toluene, acetone, acetonitrile, dioxane, tetrahydrofuran (THF), ethyl acetate, or combinations thereof.

* * * * *